US006569655B2

(12) United States Patent
Hart

(10) Patent No.: US 6,569,655 B2
(45) Date of Patent: May 27, 2003

(54) NUCLEIC ACIDS AND POLYPEPTIDES RELATED TO A GUANINE EXCHANGE FACTOR OF RHO GTPASE

(75) Inventor: Matthew J. Hart, San Francisco, CA (US)

(73) Assignee: Onyx Pharmaceuticals, Inc., Richmond, CA (US)

( * ) Notice: Subject to any disclaimer, the term of this patent is extended or adjusted under 35 U.S.C. 154(b) by 0 days.

(21) Appl. No.: 09/865,960

(22) Filed: May 25, 2001

(65) Prior Publication Data

US 2002/0192785 A1 Dec. 19, 2002

Related U.S. Application Data

(62) Division of application No. 08/943,768, filed on Oct. 6, 1997, now Pat. No. 6,238,881.
(60) Provisional application No. 60/029,979, filed on Nov. 6, 1996.

(51) Int. Cl.$^7$ ............................ C12N 9/00; C07K 17/00
(52) U.S. Cl. ...................... 435/183; 530/350; 536/23.2; 536/23.5
(58) Field of Search ................................ 435/69.1, 183; 530/350; 536/23.2, 23.5

(56) References Cited

PUBLICATIONS

Hart et al., "Identification of a Novel Guanine Nucleotide Exchange Factor for the Rho GTPase" 1996, The Journal of Biological Chemistry, vol. 271, No. 41, pp 25452–25458.

Whitehead et al., "Expression Cloning of 1sc, a Novel Oncogene with Structural Similarities . . . " 1996, The Journal of Biological Chemistry, vol. 271, No. 31, pp 18643–18650.

Hart et al., "Cellular Transformation and Guanine Nucleotide Exchange Activity are Catalyzed . . . " 1994, The Journal of Biological Chemistry, vol. 269, No. 1, pp 62–65.

Aashein et al., "Characterization, expression and chromosomal localization of a human gene . . . " 1997, Oncogene, vol. 14, pp 1747–1752.

Primary Examiner—Nashaat T. Nashed
(74) Attorney, Agent, or Firm—Gregory Giotta

(57) ABSTRACT

The present invention relates to all aspects of a guanine exchange factor (GEF), for example, a Rho-GEF, such as p115 Rho-GEF. A GEF modulates cell signaling pathways, both in in vitro and in vivo, by modulating the activity of a GTPase. By way of illustration, a p115 Rho-GEF, which modulates the activity of a Rho GTPase, is described. However, the present invention relates to other GEFs, especially other Rho-GEFs. The present invention particularly relates to an isolated p115 Rho-GEF polypeptide or fragments of it, a nucleic acid coding for p115 Rho-GEF or fragments of it, and derivatives of the polypeptide and nucleic acid. The invention also relates to methods of using such polypeptides, nucleic acids, or derivatives thereof, e.g., in therapeutics, diagnostics, and as research tools. Another aspect of the present invention involves antibodies and other ligands which recognize p115 Rho-GEF, regulators of p115 Rho-GEF activity, and methods of treating pathological conditions associated or related to a Rho GTPase.

6 Claims, 2 Drawing Sheets

```
GGGCGCCCCGCCGGTCACTTCCGCGCGGACACCAGCCTTGCAGAGCCCAGGGAGATGGAAGACTTCGCCCGAGGGGCGGCCTCCCCAGGCCCC  93
                                                      M  E  D  F  A  R  G  A  A  S  P  G  P
TCCCGGCCTGGCCTGGTTCCCGTCAGCATCATCGGGGCTGAGGATGAGGATTTTGAGAACGAGCTGGAGACAAACTCAGAAGAGCAAAACAGC 186
 S  R  P  G  L  V  P  V  S  I  I  G  A  E  D  E  D  F  E  N  E  L  E  T  N  S  E  E  Q  N  S
CAGTTCCAGAGCCTGGAGCAGGTGAAGCGGCGCCCAGCCCACCTCATGGCCCTCCTGCAGCACGTGGCCCTGCAGTTTGAGCCAGGACCCCTG 279
 Q  F  Q  S  L  E  Q  V  K  R  R  P  A  H  L  M  A  L  L  Q  H  V  A  L  Q  F  E  P  G  P  L
CTTTGCTGTCTGCATGCCGACATGCTGGGCTCACTGGGCCCCAAGGAGGCCAAGAAGGCCTTCCTGGACTTCTACCACAGCTTCCTGGAGAAG 372
 L  C  C  L  H  A  D  M  L  G  S  L  G  P  K  E  A  K │K  A  F  L  D  F  Y│ H  S  F  L  E  K
ACAGCGGTTCTCCGGGTGCCGGTCCCTCCCAACGTCGCCTTTGAACTTGACCGCACTAGGGCTGACCTCATCTCCGAGGATGTCCAGCGGCGG 465
 T  A  V  L  R  V  P  V  P  P  N  V  A  F  E  L  D  R  T  R  A  D  L  I  S  E  D  V  Q  R  R
TTCGTGCAGGAGGTGGTGCAAAGCCAGCAGGTAGCCGTGGGCCGGCAGCTGGAGGACTTCCGTTCCAAGCGGCTCATGGGCATGACGCCCTGG 558
 F  V  Q  E  V  V  C  S  Q  Q  V  A  V  G  R  Q  L  E  D  F  R  S  K  R  L  M  G  M  T  P  W
GAGCAGGAGCTGGCCCAGCTGGAGGCTTGGGTTGGGCGGGACCGAGCCAGCTACGAGGCCCGGGAGCGGCACGTGGCGGAGCGGCTGCTCATG 651
 E  Q  E  L  A  Q  L  E  A  W  V  G  R  D  R  A  S  Y  E  A  R  E  R  H  V  A  E  R  L  L  M
CACCTGGAGGAGATGCAACATACCATCTCTACCGACGAAGAAAAGAGTGCTGCCGTGGTCAACGCCATTGGGCTGTACATGCGCCACCTTGGG 744
 H  L  E  E  M  Q  H  T  I  S  T  D  E  E  K  S │A  A  V  V  N  A  I  G  L  Y  M  R│ H  L  G
GTGCGGACCAAGAGTGGAGACAAGAAGTCGGGGAGGAACTTCTTCCGGAAAAAGGTGATGGGGAACCGGCGGTCGGACGACCCTCCCAAGACC 837
 V  R  T  K  S  G  D  K  K  S  G  R  N  F  F  R  K  K  V  M  G  N  R  R  S  D  D  P  P  K  T
AAGAAGGGGCTGAGCAGCATCCTGGATGCCGCCCGCTGGAACCGGGGAGAGCCCCAGGTTCCAGATTTTCGACACCTCAAAGCAGAGGTTGAT 930
 K  K  G  L  S  S  I  L  D  A  A  R  W  N  R  G  E  P  Q  V  P  D  F  R  H  L  K  A  E  V  D
GCCGAGAAGCCAGGTGCTACAGACCGGAAGGGAGGCGTGGGGATGCCCTCTCGGGACCGGAATATCGGGGCTCCTGGGCAGGACACCCCTGGA 1023
 A  E  K  P  G  A  T  D  R  K  G  G  V  G  M  P  S  R  D  R  N  I  G  A  P  G  Q  D  T  P  G
GTCTCTCTGCACCCTCTGTCCCTGGACAGCCCAGACCGGGAACCAGGTGCTGACGCCCCCTGGAGCTGGGGGACTCATCCCCGCAGGGCCCA 1116
 V  S  L  H  P  L  S  L  D  S  P  D  R  E  P  G  A  D  A  P  L  E  L  G  D  S  S  P  Q  G  P
ATGAGCCTGGAGTCCTTGGCGCCCCCAGAGAGTACCGACGAGGGGGCCGAAACCGAGAGCCCCGAGCCTGGAGATGAGGGGGAGCCGGGGCGG 1209
 M  S  L  E  S  L  A  P  P  E  S  T  D  E  G  A  E  T  E  S  P  E  P  G  D  E  G  E  P  G  R
TCGGGACTGGAGCTTGAACCAGAAGAGCCTCCCGGCTGGCGGGAACTCGTCCCCCCAGACACCCTGCACAGCCTGCCCAAGAGCCAGGTGAAG 1302
 S  G  L  E  L  E  P  E  E  P  P  G  W  R │E  L  V  P  P  D  T  L  H  S│ L  P  K  S  Q  V  K
CGGCAGGAGGTCATCAGCGAGCTGCTGGTGACAGAGGCGGCCCACGTGCGCATGCTGCGGGTGCTGCACGACCTCTTCTTCCAGCCATGGCA 1395
│R  Q  E  V  I  S  E  L  L  V  T  E  A  A  H  V│ R  M  L  R  V  L  H  D  L  F  F  Q  P  M  A
GAATGCCTGTTCTTCCCCTTGGAGGAGCTGCAGAACATCTTCCCCAGCCTGGACGAGCTCATCGAGGTGCATTCCCTGTTCCTCGATCGCCTG 1488
 E  C  L  F  F  P  L  E  E  L  Q  N  I  F  P  S  L  D  E  L  I  E  V  H  S  L  F  L  D  R  L
ATGAAGCGGAGGCAGGAGAGTGGCTACCTCATCGAGGAGATCGGAGACGTGCTGCTGGCCCGTTTGATGGTGCTGAGGGCTCCTGGTTCCAG 1581
 M  K  R  R  Q  E  S  G  Y  L  I  E  E  I  G  D  V  L  L  A  R  F  D  G  A  E  G  S  W  F  Q
AAAATCTCCTCCCGCTTCTGCAGCCGCCAGTCATTTGCCTTAGAGCAGCTCAAAGCCAAGCAACGCAAGGACCTCGGTTCTGTGCCCTTCGTG 1674
 K  I  S  S  R  F  C  S  R  Q  S  F  A  L  E  Q  L  K  A  K  Q  R  K  D  P  R  F  C  A  F  V
CAGGAAGCTGAGAGCCGCCCGCGGTGCCGCCGCCTGCAGCTGAAGGACATGATCCCCACGGAGATGCAGCGGCTGACCAAGTACCCCCTGCTC 1767
 Q  E  A  E  S  R  P  R  C  R  R  L  Q  L  K  D  M  I  P  T  E  M  Q  R  L  T  K  Y  P  L  L
CTGCAGAGCATCGGGCAGAACACAGAAGAGCCCACAGAACGGGAGAAAGTGGAGCTGCCAGCCGAGTGCTGCCGGGAAATTCTACACCACGTC 1860
 L  Q  S  I  G  Q  N  T  E  E  P  T  E  R  E  K  V  E  L  A  A  E  C  C  R  E  I  L  H  H  V
AACCAAGCCGTGCGTGACATGGAGGACCTGCTGAGGCTCAAGGACTATCAGCGGCGCCTGGACTTGTCCCACCTTCGGCAGAGCAGCGACCCT 1953
 N  Q  A  V  R  D  M  E  D  L  L  R  L  K  D  Y  Q  R  R  L  D  L  S  H  L  R  Q  S  S  D  P
ATGCTGAGCGAGTTCAAGAACCTGGACATCACCAAGAAGAAATTGGTCCACGAGGGCCCACTGACGTGGCGGGTGACTAAGGACAAGGCAGTG 2046
 M  L  S  E  F  K  N  L  D  I  T  K  K  K  L  V  H  E  G  P  L  T  W  R  V  T  K  D  K  A  V
GAGGTGCATGTGCTGCTGCTGGACGACCTGCTGCTGCTGCTCCAGCGCCAGGACGGCGGCTGCTGCTCAAGTCCCATAGCCGGACACTGACG 2139
 E  V  H  V  L  L  L  D  D  L  L  L  L  Q  R  D  E  R  L  L  L  K  S  H  S  R  T  L  T
CCCACGCCCGATGGCAAGACCATGCTGCGGCCCGTGCTGCGGCTCACCTCCGCCATGACCCGCGAGGTGGCCACCGATCACAAAGCCTTCTAC 2232
 P  T  P  D  G  K  T  M  L  R  P  V  L  R  L  T  S  A  M  T  R  E  V  A  T  D  H  K  A  F  Y
GTCCTTTTTACCTGGGACCAGGAGGCCCAGATATACGAGCTGGTGGCACAGACTGTGTCGGAGCGGAAAAACTGGTGTGCTCTCATCACTGAG 2325
 V  L  F  T  W  D  Q  E  A  Q  I  Y  E  L  V  A  Q  T  V  S  E  R  K  N  W  C  A  L  I  T  E
ACTGCCGGATCCCTGAAAGTCCCTGCCCCTGCCTCTCGCCCTAAGCCCCGGCCCAGGCCGAGCAGCACCCGAGAACCCCTCCTCAGCAGCTCT 2418
 T  A  G  S  L  K  V  P  A  P  A  S  R  P  K  P  R  P  R  P  S  S  T  R  E  P  L  L  S  S  S
```

FIGURE 1

```
GAGAACGGGAATGGTGGCCGAGAGACGTCTCCAGCTGATGCCCGGACCGAGAGAATCCTCAGTGACCTCCTGCCCTTCTGCAGACCAGGCCCC 2511
 E   N   G   N   G   G   R   E   T   S   P   A   D   A   R   T   E   R   I   L   S   D   L   L   P   F   C   R   P   G   P
GAGGGCCAGCTCGCTGCCACGGCCCTTCGGAAAGTGCTGTCCCTGAAGCAGCTTCTGTTTCCGGCGGAGGAAGACAATGGGGCGGGGCCTCCT 2604
 E   G   Q   L   A   A   T   A   L   R   K   V   L   S   L   K   Q   L   L   F   P   A   E   E   D   N   G   A   G   P   P
CGAGATGGGGATGGGGTCCCAGGGGGCGGGCCCCTGAGCCCAGCACGGACCCAGGAAATCCAGGAGAACCTGCTCAGCTTGGAGGAGACCATG 2697
 R   D   G   D   G   V   P   G   G   G   P   L   S   P   A   R   T   Q   E   I   Q   E   N   L   L   S   L   E   E   T   M
AAGCAGCTGGAGGAGTTGGAGGAGGAATTTTGCCGCCTGAGACCCCTCCTGTCTCAGCTTGGGGGGAACTCTGTCCCCCAGCCTGGCTGCACT 2790
 K   Q   L   E   E   L   E   E   E   F   C   R   L   R   P   L   L   S   Q   L   G   G   N   S   V   P   Q   P   G   C   T
TGAGGTTCCCGCCCAGGAAGGCCTTTTGCAAGAAGGAGAGGAATGGGGGAGAGGACGTGAGGGACCACCCCCACCCACACAGCTGCCGCAGCA 2883

TCTCACACCCCGAGGGCCTGAGGAGAGGGAGCTGTGGGCCACGCCTGGGAGGGGCCCAGCTGGGGTTACTGCCCCCGCATGAGCCTCGGCCAT 2976
CTCTCCCTCCTGCCCTCTGCTTGGGGGACTCAGGGCTCCATTCTGGAGGGCACCACGGTGACCCGGGCCATCTCAGTATTGCCTGTGGGGGCC 3069
ACCCCTCCACCCCCACCCCCAAGTGCCTTCGCTCTGTTTTTATACCCTGAATTGGAGGGTTTATTTTTTAATATATATTAT 3150
```

FIGURE 1 continued

SEQUENCE LISTING

```
<160> NUMBER OF SEQ ID NOS: 12

<210> SEQ ID NO 1
<211> LENGTH: 3150
<212> TYPE: DNA
<213> ORGANISM: Human p115 GEF-Rho gene
<220> FEATURE:
<221> NAME/KEY: CDS
<222> LOCATION: (55)..(2790)
<223> OTHER INFORMATION:

<400> SEQUENCE: 1
gggcgccccg ccggtcactt ccgcgcggac accagccttg cagagcccag ggag atg      57
                                                              Met
                                                              1 gaa gac ttc gcc cga ggg gcg gcc tcc cca ggc ccc tcc cgg cct ggc     105
Glu Asp Phe Ala Arg Gly Ala Ala Ser Pro Gly Pro Ser Arg Pro Gly
        5                   10                  15 ctg gtt ccc gtc agc atc atc ggg gct gag gat gag gat ttt gag aac     153
Leu Val Pro val Ser Ile Ile Gly Ala Glu Asp Glu Asp Phe Glu Asn
    20                  25                  30 gag ctg gag aca aac tca gaa gag caa aac agc cag ttc cag agc ctg     201
Glu Leu Glu Thr Asn Ser Glu Glu Gln Asn Ser Gln Phe Gln Ser Leu
35                  40                  45 gag cag gtg aag cgg cgc cca gcc cac ctc atg gcc ctc ctg cag cac     249
Glu Gln Val Lys Arg Arg Pro Ala His Leu Met Ala Leu Leu Gln His
50                  55                  60                  65 gtg gcc ctg cag ttt gag cca gga ccc ctg ctt tgc tgt ctg cat gcc     297
Val Ala Leu Gln Phe Glu Pro Gly Pro Leu Leu Cys Cys Leu His Ala
                70                  75                  80 gac atg ctg ggc tca ctg ggc ccc aag gag gcc aag aag gcc ttc ctg     345
Asp Met Leu Gly Ser Leu Gly Pro Lys Glu Ala Lys Lys Ala Phe Leu
            85                  90                  95 gac ttc tac cac agc ttc ctg gag aag aca gcg gtt ctc cgg gtg ccg     393
Asp Phe Tyr His Ser Phe Leu Glu Lys Thr Ala Val Leu Arg Val Pro
```

-continued

```
              100                     105                     110
gtc cct ccc aac gtc gcc ttt gaa ctt gac cgc act agg gct gac ctc        441
Val Pro Pro Asn Val Ala Phe Glu Leu Asp Arg Thr Arg Ala Asp Leu
        115                     120                     125 atc tcc gag gat gtc cag cgg cgg ttc gtg cag gag gtg gtg caa agc        489
Ile Ser Glu Asp Val Gln Arg Arg Phe Val Gln Glu Val Val Gln Ser
130                     135                     140                 145 cag cag gta gcc gtg ggc cgg cag ctg gag gac ttc cgt tcc aag cgg        537
Gln Gln Val Ala Val Gly Arg Gln Leu Glu Asp Phe Arg Ser Lys Arg
                    150                     155                 160 ctc atg ggc atg acg ccc tgg gag cag gag ctg gcc cag ctg gag gct        585
Leu Met Gly Met Thr Pro Trp Glu Gln Glu Leu Ala Gln Leu Glu Ala
                165                     170                     175 tgg gtt ggg cgg gac cga gcc agc tac gag gcc cgg gag cgg cac gtg        633
Trp Val Gly Arg Asp Arg Ala Ser Tyr Glu Ala Arg Glu Arg His Val
            180                     185                     190 gcg gag cgg ctg ctc atg cac ctg gag gag atg caa cat acc atc tct        681
Ala Glu Arg Leu Leu Met His Leu Glu Glu Met Gln His Thr Ile Ser
        195                     200                     205 acc gac gaa gaa aag agt gct gcc gtg gtc aac gcc att ggg ctg tac        729
Thr Asp Glu Glu Lys Ser Ala Ala Val Val Asn Ala Ile Gly Leu Tyr
210                     215                     220                 225 atg cgc cac ctt ggg gtg cgg acc aag agt gga gac aag aag tcg ggg        777
Met Arg His Leu Gly Val Arg Thr Lys Ser Gly Asp Lys Lys Ser Gly
                    230                     235                 240 aag aac ttc ttc cgg aaa aag gtg atg ggg aac cgg cgg tcg gac gac        825
Arg Asn Phe Phe Arg Lys Lys Val Met Gly Asn Arg Arg Ser Asp Asp
                245                     250                     255 cct ccc aag acc aag aag ggg ctg agc agc atc ctg gat gcc gcc cgc        873
Pro Pro Lys Thr Lys Lys Gly Leu Ser Ser Ile Leu Asp Ala Ala Arg
            260                     265                     270 tgg aac cgg gga gag ccc cag gtt cca gat ttt cga cac ctc aaa gca        921
Trp Asn Arg Gly Glu Pro Gln Val Pro Asp Phe Arg His Leu Lys Ala
        275                     280                     285 gag gtt gat gcc gag aag cca ggt gct aca gac cgg aag gga ggc gtg        969
Glu Val Asp Ala Glu Lys Pro Gly Ala Thr Asp Arg Lys Gly Gly Val
290                     295                     300                 305 ggg atg ccc tct cgg gac cgg aat atc ggg gct cct ggg cag gac acc       1017
Gly Met Pro Ser Arg Asp Arg Asn Ile Gly Ala Pro Gly Gln Asp Thr
                    310                     315                 320 cct gga gtc tct ctg cac cct ctg tcc ctg gac agc cca gac cgg gaa       1065
Pro Gly Val Ser Leu His Pro Leu Ser Leu Asp Ser Pro Asp Arg Glu
                325                     330                     335 cca ggt gct gac gcc ccc ctg gag ctg ggg gac tca tcc ccg cag ggc       1113
Pro Gly Ala Asp Ala Pro Leu Glu Leu Gly Asp Ser Ser Pro Gln Gly
            340                     345                     350 cca atg agc ctg gag tcc ttg gcg ccc cca gag agt acc gac gag ggg       1161
Pro Met Ser Leu Glu Ser Leu Ala Pro Pro Glu Ser Thr Asp Glu Gly
        355                     360                     365 gcc gaa acc gag agc ccc gag cct gga gat gag ggg gag ccg ggg cgg       1209
Ala Glu Thr Glu Ser Pro Glu Pro Gly Asp Glu Gly Glu Pro Gly Arg
370                     375                     380                 385 tcg gga ctg gag ctt gaa cca gaa gag cct ccc ggc tgg cgg gaa ctc       1257
Ser Gly Leu Glu Leu Glu Pro Glu Glu Pro Pro Gly Trp Arg Glu Leu
                    390                     395                 400 gtc ccc cca gac acc ctg cac agc ctg ccc aag agc cag gtg aag cgg       1305
Val Pro Pro Asp Thr Leu His Ser Leu Pro Lys Ser Gln Val Lys Arg
                405                     410                     415 cag gag gtc atc agc gag ctg ctg gtg aca gag gcg gcc cac gtg cgc       1353
```

```
                    Gln Glu Val Ile Ser Glu Leu Leu Val Thr Glu Ala Ala His Val Arg
                        420                 425                 430 atg ctg cgg gtg ctg cac gac ctc ttc ttc cag ccc atg gca gaa tgc      1401
Met Leu Arg Val Leu His Asp Leu Phe Phe Gln Pro Met Ala Glu Cys
    435                 440                 445 ctg ttc ttc ccc ttg gag gag ctg cag aac atc ttc ccc agc ctg gac      1449
Leu Phe Phe Pro Leu Glu Glu Leu Gln Asn Ile Phe Pro Ser Leu Asp
450                 455                 460                 465 gag ctc atc gag gtg cat tcc ctg ttc ctc gat cgc ctg atg aag cgg      1497
Glu Leu Ile Glu Val His Ser Leu Phe Leu Asp Arg Leu Met Lys Arg
                    470                 475                 480 agg cag gag agt ggc tac ctc atc gag gag atc gga gac gtg ctg ctg      1545
Arg Gln Glu Ser Gly Tyr Leu Ile Glu Glu Ile Gly Asp Val Leu Leu
                485                 490                 495 gcc cgg ttt gat ggt gct gag ggc tcc tgg ttc cag aaa atc tcc tcc      1593
Ala Arg Phe Asp Gly Ala Glu Gly Ser Trp Phe Gln Lys Ile Ser Ser
            500                 505                 510 cgc ttc tgc agc cgc cag tca ttt gcc tta gag cag ctc aaa gcc aag      1641
Arg Phe Cys Ser Arg Gln Ser Phe Ala Leu Glu Gln Leu Lys Ala Lys
        515                 520                 525 caa cgc aag gac cct cgg ttc tgt gcc ttc gtg cag gaa gct gag agc      1689
Gln Arg Lys Asp Pro Arg Phe Cys Ala Phe Val Gln Glu Ala Glu Ser
530                 535                 540                 545 cgc ccg cgg tgc cgc cgc ctg cag ctg aag gac atg atc ccc acg gag      1737
Arg Pro Arg Cys Arg Arg Leu Gln Leu Lys Asp Met Ile Pro Thr Glu
                    550                 555                 560 atg cag cgg ctg acc aag tac ccc ctc ctc ctg cag agc atc ggg cag      1785
Met Gln Arg Leu Thr Lys Tyr Pro Leu Leu Leu Gln Ser Ile Gly Gln
                565                 570                 575 aac aca gaa gag ccc aca gaa cgg gag aaa gtg gag ctg gca gcc gag      1833
Asn Thr Glu Glu Pro Thr Glu Arg Glu Lys Val Glu Leu Ala Ala Glu
            580                 585                 590 tgc tgc cgg gaa att cta cac cac gtc aac caa gcc gtg cgt gac atg      1881
Cys Cys Arg Glu Ile Leu His His Val Asn Gln Ala Val Arg Asp Met
        595                 600                 605 gag gac ctg ctg agg ctc aag gac tat cag cgg cgc ctg gac ttg tcc      1929
Glu Asp Leu Leu Arg Leu Lys Asp Tyr Gln Arg Arg Leu Asp Leu Ser
610                 615                 620                 625 cac ctt cgg cag agc agc gac cct atg ctg agc gag ttc aag aac ctg      1977
His Leu Arg Gln Ser Ser Asp Pro Met Leu Ser Glu Phe Lys Asn Leu
                    630                 635                 640 gac atc acc aag aag aaa ttg gtc cac gag ggc cca ctg acg tgg cgg      2025
Asp Ile Thr Lys Lys Lys Leu Val His Glu Gly Pro Leu Thr Trp Arg
                645                 650                 655 gtg act aag gac aag gca gtg gag gtg cat gtg ctg ctg ctg gac gac      2073
Val Thr Lys Asp Lys Ala Val Glu Val His Val Leu Leu Leu Asp Asp
            660                 665                 670 ctg ctg ctg ctc cag cgc cag gac gag cgg ctg ctc ctc aag tcc          2121
Leu Leu Leu Leu Gln Arg Gln Asp Glu Arg Leu Leu Leu Lys Ser
        675                 680                 685 cat agc cgg aca ctg acg ccc acg ccc gat ggc aag acc atg ctg cgg      2169
His Ser Arg Thr Leu Thr Pro Thr Pro Asp Gly Lys Thr Met Leu Arg
690                 695                 700                 705 ccc gtg ctg cgg ctc acc tcc gcc atg acc cgc gag gtg gcc acc gat      2217
Pro Val Leu Arg Leu Thr Ser Ala Met Thr Arg Glu Val Ala Thr Asp
                    710                 715                 720 cac aaa gcc ttc tac gtc ctt ttt acc tgg gac cag gag gcc cag ata      2265
His Lys Ala Phe Tyr Val Leu Phe Thr Trp Asp Gln Glu Ala Gln Ile
                725                 730                 735
```

-continued

```
tac gag ctg gtg gca cag act gtg tcg gag cgg aaa aac tgg tgt gct    2313
Tyr Glu Leu Val Ala Gln Thr Val Ser Glu Arg Lys Asn Trp Cys Ala
        740                 745                 750 ctc atc act gag act gcc gga tcc ctg aaa gtc cct gcc cct gcc tct    2361
Leu Ile Thr Glu Thr Ala Gly Ser Leu Lys Val Pro Ala Pro Ala Ser
    755                 760                 765 cgc cct aag ccc cgg ccc agg ccg agc agc acc cga gaa ccc ctc ctc    2409
Arg Pro Lys Pro Arg Pro Arg Pro Ser Ser Thr Arg Glu Pro Leu Leu
770                 775                 780                 785 agc agc tct gag aac ggg aat ggt ggc cga gag acg tct cca gct gat    2457
Ser Ser Ser Glu Asn Gly Asn Gly Gly Arg Glu Thr Ser Pro Ala Asp
                790                 795                 800 gcc cgg acc gag aga atc ctc agt gac ctc ctg ccc ttc tgc aga cca    2505
Ala Arg Thr Glu Arg Ile Leu Ser Asp Leu Leu Pro Phe Cys Arg Pro
            805                 810                 815 ggc ccc gag ggc cag ctc gct gcc acg gcc ctt cgg aaa gtg ctg tcc    2553
Gly Pro Glu Gly Gln Leu Ala Ala Thr Ala Leu Arg Lys Val Leu Ser
        820                 825                 830 ctg aag cag ctt ctg ttt ccg gcg gag gaa gac aat ggg gcg ggg cct    2601
Leu Lys Gln Leu Leu Phe Pro Ala Glu Glu Asp Asn Gly Ala Gly Pro
    835                 840                 845 cct cga gat ggg gat ggg gtc cca ggg ggc ggg ccc ctg agc cca gca    2649
Pro Arg Asp Gly Asp Gly Val Pro Gly Gly Gly Pro Leu Ser Pro Ala
850                 855                 860                 865 cgg acc cag gaa atc cag gag aac ctg ctc agc ttg gag gag acc atg    2697
Arg Thr Gln Glu Ile Gln Glu Asn Leu Leu Ser Leu Glu Glu Thr Met
                870                 875                 880 aag cag ctg gag gag ttg gag gag gaa ttt tgc cgc ctg aga ccc ctc    2745
Lys Gln Leu Glu Glu Leu Glu Glu Glu Phe Cys Arg Leu Arg Pro Leu
            885                 890                 895 ctg tct cag ctt ggg ggg aac tct gtc ccc cag cct ggc tgc act        2790
Leu Ser Gln Leu Gly Gly Asn Ser Val Pro Gln Pro Gly Cys Thr
        900                 905                 910 tgaggttccc gcccaggaag gccttttgca agaaggagag gaatggggga gaggacgtga   2850
gggaccaccc ccaccacaca gctgccgca gcatctcaca ccccgagggc ctgaggagag    2910
ggagctgtgg gccacgcctg ggaggggccc agctggggtt actgccccg catgagcctc    2970 ggccatctct ccctcctgcc ctctgcttgg gggactcagg gctccattct ggagggcacc   3030
acggtgaccc gggccatctc agtattgctt gtggggggcca cccctccacc cccacccca   3090 agtgccttcg ctctgttttt ataccctgaa ttggagggtt tattttttaa tatatattat   3150
```

<210> SEQ ID NO 2
<211> LENGTH: 912
<212> TYPE: PRT
<213> ORGANISM: Human p115 GEF-Rho gene
<220> FEATURE:

<400> SEQUENCE: 2

```
Met Gly Asp Phe Ala Arg Gly Ala Ala Ser Pro Gly Pro Ser Arg Pro
1               5                   10                  15

Gly Leu Val Pro Val Ser Ile Ile Gly Ala Glu Asp Glu Asp Phe Glu
            20                  25                  30

Asn Glu Leu Glu Thr Asn Ser Glu Glu Gln Asn Ser Gln Phe Gln Ser
        35                  40                  45

Leu Glu Gln Val Lys Arg Arg Pro Ala His Leu Met Ala Leu Leu Gln
    50                  55                  60

His Val Ala Leu Gln Phe Glu Pro Gly Pro Leu Leu Cys Cys Leu His
65                  70                  75                  80
```

```
Ala Asp Met Leu Gly Ser Leu Gly Pro Lys Glu Ala Lys Lys Ala Phe
                 85                  90                  95
Leu Asp Phe Tyr His Ser Phe Leu Glu Lys Thr Ala Val Leu Arg Val
            100                 105                 110
Pro Val Pro Pro Asn Val Ala Phe Glu Leu Asp Arg Thr Arg Ala Asp
            115                 120                 125
Leu Ile Ser Glu Asp Val Gln Arg Arg Phe Val Gln Glu Val Val Gln
        130                 135                 140
Ser Gln Gln Val Ala Val Gly Arg Gln Leu Glu Asp Phe Arg Ser Lys
145                 150                 155                 160
Arg Leu Met Gly Met Thr Pro Trp Glu Gln Glu Leu Ala Gln Leu Glu
                165                 170                 175
Ala Trp Val Gly Arg Asp Arg Ala Ser Tyr Glu Ala Arg Glu Arg His
                180                 185                 190
Val Ala Glu Arg Leu Leu Met His Leu Glu Glu Met Gln His Thr Ile
            195                 200                 205
Ser Thr Asp Glu Glu Lys Ser Ala Ala Val Val Asn Ala Ile Gly Leu
        210                 215                 220
Tyr Met Arg His Leu Gly Val Arg Thr Lys Ser Gly Asp Lys Lys Ser
225                 230                 235                 240
Gly Arg Asn Phe Phe Arg Lys Lys Val Met Gly Asn Arg Arg Ser Asp
                245                 250                 255
Asp Pro Pro Lys Thr Lys Lys Gly Leu Ser Ser Ile Leu Asp Ala Ala
                260                 265                 270
Arg Trp Asn Arg Gly Glu Pro Gln Val Pro Asp Phe Arg His Leu Lys
                275                 280                 285
Ala Glu Val Asp Ala Glu Lys Pro Gly Ala Thr Asp Arg Lys Gly Gly
            290                 295                 300
Val Gly Met Pro Ser Arg Asp Arg Asn Ile Gly Ala Pro Gly Gln Asp
305                 310                 315                 320
Thr Pro Gly Val Ser Leu His Pro Leu Ser Leu Asp Ser Pro Asp Arg
                325                 330                 335
Glu Pro Gly Ala Asp Ala Pro Leu Glu Leu Gly Asp Ser Ser Pro Gln
                340                 345                 350
Gly Pro Met Ser Leu Glu Ser Leu Ala Pro Pro Glu Ser Thr Asp Glu
                355                 360                 365
Gly Ala Glu Thr Glu Ser Pro Gly Pro Gly Asp Glu Gly Glu Pro Gly
            370                 375                 380
Arg Ser Gly Leu Glu Leu Glu Pro Glu Glu Pro Pro Gly Trp Arg Glu
385                 390                 395                 400
Leu Val Pro Pro Asp Thr Leu His Ser Leu Pro Lys Ser Gln Val Lys
                405                 410                 415
Arg Gln Glu Val Ile Ser Glu Leu Leu Val Thr Glu Ala Ala His Val
            420                 425                 430
Arg Met Leu Arg Val Leu His Asp Leu Phe Gln Pro Met Ala Glu
            435                 440                 445
Cys Leu Phe Phe Pro Leu Glu Glu Leu Gln Asn Ile Phe Pro Ser Leu
            450                 455                 460
Asp Glu Leu Ile Glu Val His Ser Leu Phe Leu Asp Arg Leu Met Lys
465                 470                 475                 480
Arg Arg Gln Glu Ser Gly Tyr Leu Ile Glu Glu Ile Gly Asp Val Leu
                485                 490                 495
```

-continued

```
Leu Ala Arg Phe Asp Gly Ala Glu Gly Ser Trp Phe Gln Lys Ile Ser
            500                 505                 510
Ser Arg Phe Cys Ser Arg Gln Ser Phe Ala Leu Glu Gln Leu Lys Ala
        515                 520                 525
Lys Gln Arg Lys Asp Pro Arg Phe Cys Ala Phe Val Gln Glu Ala Glu
    530                 535                 540
Ser Arg Pro Arg Cys Arg Arg Leu Gln Leu Lys Asp Met Ile Pro Thr
545                 550                 555                 560
Glu Met Gln Arg Leu Thr Lys Tyr Pro Leu Leu Gln Ser Ile Gly
                565                 570                 575
Gln Asn Thr Glu Glu Pro Thr Glu Arg Glu Lys Val Glu Leu Ala Ala
            580                 585                 590
Glu Cys Cys Arg Glu Ile Leu His His Val Asn Gln Ala Val Arg Asp
        595                 600                 605
Met Glu Asp Leu Leu Arg Leu Lys Asp Tyr Gln Arg Arg Leu Asp Leu
    610                 615                 620
Ser His Leu Arg Gln Ser Ser Asp Pro Met Leu Ser Glu Phe Lys Asn
625                 630                 635                 640
Leu Asp Ile Thr Lys Lys Lys Leu Val His Glu Gly Pro Leu Thr Trp
                645                 650                 655
Arg Val Thr Lys Asp Lys Ala Val Glu Val His Val Leu Leu Leu Asp
            660                 665                 670
Asp Leu Leu Leu Leu Gln Arg Gln Asp Glu Arg Leu Leu Leu Lys
        675                 680                 685
Ser His Ser Arg Thr Leu Thr Pro Thr Pro Asp Gly Lys Thr Met Leu
    690                 695                 700
Arg Pro Val Leu Arg Leu Thr Ser Ala Met Thr Arg Glu Val Ala Thr
705                 710                 715                 720
Asp His Lys Ala Phe Tyr Val Leu Phe Thr Trp Asp Gln Glu Ala Gln
                725                 730                 735
Ile Tyr Glu Leu Val Ala Gln Thr Val Ser Glu Arg Lys Asn Trp Cys
            740                 745                 750
Ala Leu Ile Thr Glu Thr Ala Gly Ser Leu Lys Val Pro Ala Pro Ala
        755                 760                 765
Ser Arg Pro Lys Pro Arg Pro Arg Pro Ser Ser Thr Arg Glu Pro Leu
    770                 775                 780
Leu Ser Ser Ser Glu Asn Gly Asn Gly Gly Arg Glu Thr Ser Pro Ala
785                 790                 795                 800
Asp Ala Arg Thr Glu Arg Ile Leu Ser Asp Leu Leu Pro Phe Cys Arg
                805                 810                 815
Pro Gly Pro Glu Gly Gln Leu Ala Ala Thr Ala Leu Arg Lys Val Leu
            820                 825                 830
Ser Leu Lys Gln Leu Leu Phe Pro Ala Glu Glu Asp Asn Gly Ala Gly
        835                 840                 845
Pro Pro Arg Asp Gly Asp Gly Val Pro Gly Gly Pro Leu Ser Pro
    850                 855                 860
Ala Arg Thr Gln Glu Ile Gln Glu Asn Leu Leu Ser Leu Glu Glu Thr
865                 870                 875                 880
Met Lys Gln Leu Glu Glu Leu Glu Glu Glu Phe Cys Arg Leu Arg Pro
                885                 890                 895
Leu Leu Ser Gln Leu Gly Gly Asn Ser Val Pro Gln Pro Gly Cys Thr
            900                 905                 910
```

```
<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
gagtctctct gcaccctctg                                                 20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
cacgtctccg atctcctcga                                                 20

<210> SEQ ID NO 5
<211> LENGTH: 14
<212> TYPE: DNA
<213> ORGANISM: Artificial Sequence
<220> FEATURE:
<223> OTHER INFORMATION: Oligonucleotide

<400> SEQUENCE: 5
ggaaccggcg gacg                                                       14

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
aagatgttct gcagctcctc                                                 20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
gagtctctct gcaccctctg                                                 20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
cacgtctccg atctcctcga                                                 20

<210> SEQ ID NO 9
<211> LENGTH: 14
<212> TYPE: DNA
<213> ORGANISM: Artificial Sequence
<220> FEATURE:
<223> OTHER INFORMATION: Oligonucleotide
```

-continued

```
<400> SEQUENCE: 9
ggaaccggcg gacg                                                              14

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
aagatgttct gcagctcctc                                                        20

<210> SEQ ID NO 11
<211> LENGTH: 47
<212> TYPE: DNA
<213> ORGANISM: Artificial Sequence
<220> FEATURE:
<223> OTHER INFORMATION: Oligonucleotide

<400> SEQUENCE: 11
cggcaggagg tgatctctga gctgctggtg acagaggctg cccatgt                          47

<210> SEQ ID NO 12
<211> LENGTH: 16
<212> TYPE: PRT
<213> ORGANISM: Artificial Sequence
<220> FEATURE:
<223> OTHER INFORMATION: Peptide

<400> SEQUENCE: 12

Arg Gln Glu Val Ile Ser Glu Leu Leu Val Thr Glu Ala Ala His Val
1               5                   10                  15
```

NUCLEIC ACIDS AND POLYPEPTIDES RELATED TO A GUANINE EXCHANGE FACTOR OF RHO GTPASE

This application is a divisional of U.S. patent application Ser. No. 08/943,768, filed Oct. 6, 1997, now U.S. Pat. No. 6,238,881 which claims priority from U.S. Provisional Application No. 60/029,979, filed Nov. 6, 1996.

BACKGROUND OF THE INVENTION

Members of the Ras superfamily regulate diverse signalling pathways. The prototype of this family, Ras, is involved in regulating cell growth and differentiation (1). The Rho subfamily (Rho, Rac, Cdc42) are also involved in regulating cell growth as well as controlling the formation of focal contacts and alterations in the actin cytoskeleton which occur upon growth factor stimulation (2,3,4,5,6,7). Common to all Ras family members is their ability to cycle between inactive (GDP bound) and active (GTP bound) states. In this regard, these GTPases act as molecular switches, capable of processing information and then disseminating that information to control a specific pathway.

This property of cycling between GTP and GDP states has provided a means to identify and purify proteins which regulate the nucleotide state of Ras and Ras-related GTPases (1). By monitoring the hydrolysis of GTP to GDP, GTPase activating proteins (GAPs) have been characterized for many members of the Ras family (1,8,9). Guanine nucleotide dissociation inhibitors (GDIs) were identified based on their ability to inhibit the dissociation of GDP. It has subsequently been determined that they also bind to the GTP state, inhibiting the intrinsic and GAP stimulated GTP hydrolysis (1). In general, GAPs and effectors have a high affinity for the GTP-bound state, while GDI proteins bind most tightly to the GDP-bound state. These properties have been exploited to purify effectors for Cdc42Hs (10,11,12), Ras (13,14) and Rho (15,16). An affinity approach has also been employed with Cdc42Hs-GTP and has led to the characterization of IQGAP1, a potential mediator for observed cytoskeletal events induced by Cdc42 (17).

A modification of this affinity approach can also be used to identify and purify guanine nucleotide exchange factors (GEFs). GEFs can be distinguished from other regulatory proteins by their ability to interact preferentially with the nucleotide-depleted state of G-proteins (18,19). By stimulating the dissociation of GDP and subsequent binding of GTP, GEFs play an important role in the activation of Ras-like proteins. For example, Ras is converted to its GTP-bound form by the growth-factor stimulated translocation of Sos, a Ras-specific GEF (20). The characterization of GEFs that specifically activate Rho family members will help elucidate signalling pathways in which these GTPases participate. By incubating lysates with nucleotide-depleted Rho, we have purified a Rho specific GEF and isolated a cDNA coding for the 115 kDa protein, which is homologous to the dbl (21) and lbc oncogenes (22).

DESCRIPTION OF THE INVENTION

The present invention relates to all aspects of a guanine exchange factor (GEF), in particular, a Rho-GEF, such as p115 Rho-GEF. A GEF modulates cell signaling pathways, both in vitro and in vivo, by modulating the activity of a GTPase. By way of illustration, a p115 Rho-GEF, which modulates the activity of a RhoA GTPase, is described. However, the present invention relates to other GEFs, especially other Rho-GEFs. The present invention particularly relates to an isolated p115 Rho-GEF polypeptide or fragments of it, a nucleic acid coding for p115 Rho-GEF or fragments of it, and derivatives of the polypeptide and nucleic acid. The invention also relates to methods of using such polypeptides, nucleic acids, or derivatives thereof, e.g., in therapeutics, diagnostics, and as research tools. Another aspect of the present invention involves antibodies and other ligands which recognize p115 Rho-GEF, regulators of p115 Rho-GEF activity and other GEFs, and methods of treating pathological conditions associated or related to a Rho GTPase. The invention also relates to methods of testing for and/or identifying agents which regulate GEF by measuring their effect on GEF activity, e.g., in binding to a GTPase and/or nucleotide exchange activity.

BRIEF DESCRIPTION OF THE DRAWINGS

FIG. 1 shows the complete nucleotide sequence (SEQ ID NO: 1) and deduced amino acid sequence (SEQ ID NO: 2) for a polypeptide encoded for by a human p115 GEF-Rho gene.

DETAILED DESCRIPTION OF THE INVENTION

In accordance with the present invention, a novel polypeptide and nucleic acid coding for a p115 Rho-GEF has been identified and isolated. As used herein, p115 Rho-GEF means a polypeptide, or a nucleic acid coding for a p115 Rho-GEF polypeptide, which polypeptide has a specific binding affinity for a guanine nucleotide-depleted state of G-proteins (in particular RhoA), a guanine nucleotide exchange activity, an oncogenic transforming activity, and an immunogenic activity. By specific binding affinity, it is meant that the polypeptide has a binding preference for the nucleotide-depleted state of the G-protein, in contrast, e.g., to the GDP- or GTP-bound state of the G-protein which is preferentially bound by other regulatory proteins. By guanine nucleotide exchange activity, it is meant that the polypeptide stimulates or catalyzes the dissociation of GDP from a G-protein, such as Rho, and subsequent binding of GTP. By cellular oncogenic transforming activity, it is meant that introduction of a nucleic acid coding for p115 Rho-GEF into a cell line, e.g., NIH 3T3 cells, confers a transformed phenotype on such cells. A transformed phenotype can be measured by foci formation, e.g., as characterized and described by Eva and Aaronson, Nature, 316:273-276, 1985. Immunogenic activity means that the polypeptide binds to p115 Rho-GEF specific antibodies or is capable of eliciting an immune response specific for a p115 Rho-GEF. Immunogenic activities are discussed below. The above-mentioned activities of a p115 Rho-GEF polypeptide can be assayed, e.g., as described below in the examples or according to methods which the skilled worker would know. A p115 Rho-GEF polypeptide, or corresponding nucleic acid coding for it, means a polypeptide which can be isolated from a natural source. It therefore includes naturally-occurring normal and mutant alleles. Natural sources include, e.g., living cells obtained from tissues and whole organisms, and cultured cell lines.

A human p115 Rho-GEF has an approximate molecular weight of 115 kilodaltons and contains 912 amino acids as set forth in FIG. 1 (SEQ ID NO: 2). It, or its corresponding gene, can be isolated from natural sources. Characterization of a human p115 Rho-GEF is described below and in the examples.

The present invention also relates to polypeptide fragments of p115 Rho-GEF. The fragments are preferably biologically-active. By biologically-active, it is meant that the polypeptide fragment possesses an activity in a living system or with components of a living system. Biological-activities include: a specific binding affinity for a guanine nucleotide-depleted state of G-proteins, in particular RhoA, a guanine nucleotide exchange activity, an oncogenic transforming activity, an immunogenic activity, modulating the binding between a Rho-GEF and a Rho GTPase, or acting as an agonist or antagonist of Rho GTPase activity. Such activities can be assayed routinely, e.g., according to the methods described above and below. Various fragments can be prepared. For example, a polypeptide (ΔN-p115) having amino acid 249 to 912 as set forth in FIG. 1 (SEQ ID NO: 2) has a specific binding affinity for a guanine nucleotide depleted Rho, a guanine nucleotide exchange activity, a cellular transforming activity, and an immunogenic activity. See examples below for further discussion. Fragments can also be selected in which one or more of the mentioned activities are eliminated or altered when compared to p115 Rho-GEF. As described in the examples, such fragments can be prepared routinely, e.g., by recombinant means or by proteolytic cleavage of isolated polypeptides, and then assayed for a desired activity. Table 1 below shows oncogenic transforming activity associated with various fragments of p115 Rho-GEF. As illustrated below, deletion of the N-terminal 1–82 amino acids of p115 Rho-GEF to form a polypeptide having amino acids 83–912 of FIG. 1 (SEQ ID NO: 2) eliminates transforming activity. On the other hand, a larger deletion (249–912) restores transforming activity (ΔN-p115). In another fragment (ΔN-p115 Δc) having amino acids N-terminal and C-terminal amino acids deleted, transforming activity was increased in comparison to other fragments. The mentioned N- and C-terminal truncations, however, do not substantially effect the guanine nucleotide exchange activity.

The present invention also relates to a human p115 Rho-GEF specific amino acid sequence selected from the sequence of amino acid 1 to 912 as set forth in FIG. 1 (SEQ ID NO: 2). A clone having such sequence has been deposited on Sep. 10, 1996 at the ATCC as No. 98164. A p115 Rho-GEF specific amino acid sequence means a defined amino acid sequence which is found in the recited p115 Rho-GEF sequence but not in another amino acid sequence. A specific amino acid sequence can be found routinely, e.g., by searching a gene/protein database using the BLAST set of computer programs. Such specific sequences include, e.g., amino acid 803–912. A p115 Rho-GEF specific amino acid sequence can be useful to produce peptides as antigens to generate an immune response specific for p115 Rho-GEF. Antibodies obtained by such immunization can be used as a specific probe for the p115 Rho-GEF protein for diagnostic or research purposes. Such peptides can also be used to inhibit the p115 Rho-GEF binding to Rho to modulate pathological conditions in cells.

A polypeptide of the invention, e.g., having a polypeptide sequence as shown in FIG. 1 (SEQ ID NO: 2), can by analyzed by available methods to identify structural and/or functional domains in the polypeptide. For example, when the polypeptide coding sequence set forth in FIG. 1 (SEQ ID NO: 2) is analyzed by computer algorithms, a continuous coding sequence comprising the following domains is identified: Collagen-like coiled coil, amino acid 1 to 410; Dbl homology domain, amino acid 420 to 637; pleckstrin homology domain, amino acid 646 to 762. Various programs can be employed to analyze structure of the polypeptide, including, EMBL Protein Predict; Rost and Sander, Proteins, 19:55–72, 1994; Kyte and Doolittle, J. Mol. Bio.: 157:105, 1982.

A polypeptide of the present invention can also have 100% or less amino acid sequence identity to the amino acid sequence set forth in SEQ ID NO: 2. For the purposes of the following discussion: Sequence identity means that the same nucleotide or amino acid which is found in the sequence set forth in FIG. 1. (SEQ ID NO: 1 and SEQ ID NO: 2) is found at the corresponding position of the compared sequence(s). A polypeptide having less than 100% sequence identify to the amino acid sequence set forth in FIG. 1 can be substituted in various ways, e.g., by a conservative amino acid. See below for examples of conservative amino acid substitution. The sum of the identical and conserved residues divided by the total number of residues in the sequence over which the p115 Rho-GEF polypeptide is compared is equal to the percent sequence similarity. For purposes of calculating sequence identity and similarity, the compared sequences can be aligned and calculated according to any desired method, algorithm, computer program, etc., including, e.g., FASTA, BLASTA. A polypeptide having less than 100% amino acid sequence identity to the amino acid sequence of FIG. 1 (SEQ ID NO: 2) can comprise e.g., about 60, 65, more preferably, 67, 70, 78, 80, 90, 92, 96, 99, etc.

A p115 GEF polypeptide, fragment, or substituted p115 GEF polypeptide can also comprise various modifications, where such modifications include glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

A mutation to a p115 Rho-GEF polypeptide can be selected to have a biological activity of p115 Rho-GEF, e.g., a specific binding affinity for a guanine nucleotide-depleted state of G-proteins, in particular RhoA, a guanine nucleotide exchange activity, an oncogenic transforming activity, and an immunogenic activity. The selection and preparation of mutations of p115 Rho-GEF is discussed below.

Polypeptides of the present invention (e.g., p115 Rho-GEF, fragments thereto, mutations thereof) can be used in various ways, e.g., as immunogens for antibodies as described below, as biologically-active agents (e.g., having one or more of the activities associated with p115 Rho-GEF), as inhibitors of p115 Rho-GEF. For example, upon binding of p115 Rho-GEF to Rho, a cascade of events is initiated in the cell, e.g., promoting cell proliferation and/or cytoskeletal rearrangements. The interaction between Rho-GEF and Rho can be modulated by using a peptide fragment of p115 Rho-GEF, e.g., a peptide fragment which is an inhibitor at the site where p115 Rho-GEF interacts (e.g., binds) to Rho. Such a fragment can be useful for modulating pathological conditions associated with the Rho signaling pathway. A useful fragment can be identified routinely by testing the ability of overlapping fragments of the entire length of p115 Rho-GEF to inhibit a p115 Rho-GEF activity, such as guanine nucleotide exchange activity, binding to a guanine nucleotide depleted state of Rho, and oncogenic transforming activity. The measurement of these activities is described below and in the examples. These peptides can also be identified and prepared as described in EP 496 162. Peptides can be chemically-modified, etc.

A polypeptide coding for a p115 Rho-GEF polypeptide, or a derivative or fragment thereof, can be combined with one or more structural domains, functional domains, detectable domains, antigenic domains, and/or a desired polypeptides of interest, in an arrangement which does not occur in nature, i.e., not naturally-occurring, e.g., as in a normal p115 Rho-GEF gene, a genomic fragment prepared from the genome of a living organism, e.g., an animal, preferably a mammal, such as human, mouse, or cell lines thereof. A polypeptide comprising such features is a chimeric or fusion polypeptide. Such a chimeric polypeptide can be prepared according to various methods, including, chemical, synthetic, quasi-synthetic, and/or recombinant methods. Achimeric nucleic acid coding for a chimeric polypeptide can contain the various domains or desired polypeptides in a continuous or interrupted open reading frame, e.g., containing introns, splice sites, enhancers, etc. Thechimeric nucleic acid can be produced according to various methods. See, e.g., U.S. Pat. No. 5,439,819. Adomain or desired polypeptide can possess any desired property, including, a biological function such as catalytic, signalling, growth promoting, cellular targeting, etc., a structural function such as hydrophobic, hydrophilic, membrane-spanning, etc., receptor-ligand functions, and/or detectable functions, e.g., combined with enzyme, fluorescent polypeptide, green fluorescent protein GFP (Chalfie et al., 1994, *Science*, 263:802; Cheng et al., 1996, *Nature Biotechnology*, 14:606; Levy et al., 1996, *Nature Biotechnology*, 14:610, etc. In addition, a p115 Rho-GEF nucleic acid, or a part of it, can be used as selectable marker when introduced into a host cell. For example, a nucleic acid coding for an amino acid sequence according to the present invention can be fused in-frame to a desired coding sequence and act as a tag for purification, selection, or marking purposes. The region of fusion encodes a cleavage site.

A polypeptide according to the present invention can be produced in an expression system, e.g., in vivo, in vitro, cell-free, recombinant, cell fusion, etc., according to the present invention. Modifications to the polypeptide imparted by such system include, glycosylation, amino acid substitution (e.g., by differing codon usage), polypeptide processing such as digestion, cleavage, endopeptidase or exopeptidase activity, attachment of chemical moieties, including lipids, phosphates, etc. For example, some cell lines can remove the terminal methionine from an expressed polypeptide.

A polypeptide according to the present invention can be recovered from natural sources, transformed host cells (culture medium or cells) according to the usual methods, including, ammonium sulfate or ethanol precipitation, acid extraction, anion or cation exchange chromatography, phosphocellulose chromatography, hydrophobic interaction chromatography, hydroxyapatite chromatography and lectin chromatography. It may be useful to have low concentrations (approximately 0.1–5 mM) of calcium ion present during purification (Price, et al., *J. Biol. Chem.*, 244:917 (1969)). Protein refolding steps can be used, as necessary, in completing the configuration of the mature protein. Finally, high performance liquid chromatography (HPLC) can be employed for final purification steps.

In accordance with the present invention, a nucleic acid coding for a p115 Rho-GEF can comprise, e.g., the complete coding sequence from amino acid 1 to amino acid 912 as set forth in FIG. 1 (SEQ ID NO: 1). A nucleic acid according to the present invention can also comprise a nucleotide sequence which is 100% complementary, e.g., an anti-sense, to any nucleotide sequence mentioned above and below.

A nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell at a particular stage of development, having a desired genotype, phenotype (e.g., an oncogenically transformed cell or a cancerous cell), etc.

A nucleic acid comprising a nucleotide sequence coding for a polypeptide according to the present invention can include only coding sequence of p115 Rho-GEF; coding sequence of p115 Rho-GEF and additional coding sequence (e.g., sequences coding for leader, secretory, targeting, enzymatic, fluorescent or other diagnostic peptides), coding sequence of p115 Rho-GEF and non-coding sequences, e.g., untranslated sequences at either a 5' or 3' end, or dispersed in the coding sequence, e.g., introns. A nucleic acid comprising a nucleotide sequence coding without interruption for a p115 Rho-GEF polypeptide means that the nucleotide sequence contains an amino acid coding sequence for a p115 Rho-GEF polypeptide, with no non-coding nucleotides interrupting or intervening in the coding sequence, e.g., absent intron(s). Such a nucleotide sequence can also be described as contiguous.

A nucleic acid according to the present invention also can comprise an expression control sequence operably linked to a nucleic acid as described above. The phrase "expression control sequence" means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids which hybridize to a nucleic acid comprising a nucleotide sequence as set forth in FIG. 1 (SEQ ID NO: 1). A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIG. 1 (SEQ ID NO: 1). A nucleic acid capable of hybridizing to such sequence, preferably, possesses 50%, more preferably, 70% complementarity, between the sequences. The present invention particularly relates to DNA sequences which hybridize to the nucleotide sequence set forth in FIG. 1 (SEQ ID NO: 1) under stringent conditions. As used here, "stringent conditions" means any conditions in which hybridization will occur where there is at least about 95%, preferably 97%, nucleotide complementarity between the nucleic acids. Such conditions include, e.g., hybridization for Northern: 5×SSPE, 10×Denhardts solution, 100 µg/ml freshly denatured and sheared salmon sperm DNA, 50% formamide, 2% SDS at 42° C.; hybridization for cloning from cDNA library: 1×PAM, 0.1% SDS, 50% formamide at 42° C. The present invention thus also relates to a nucleic acid of about 7 kb expressed in, e.g., heart, brain, placenta, lung, liver, skeletal muscle, kidney, pancreas, spleen, thymus, prostate, testis, ovary, small intestine, colon, and peripheral blood leukocytes. It also relates to a nucleic acid of about 7.3 kb expressed in, e.g., heart and skeletal muscle but not in the other above-mentioned tissues.

According to the present invention, a nucleic acid or polypeptide can comprise one or more differences in the nucleotide or amino acid sequence set forth in FIG. 1 (SEQ ID NO: 1 and SEQ ID NO: 2). Changes or modifications to the nucleotide and/or amino acid sequence can be accomplished by any method available, including directed or random mutagenesis.

A nucleic acid coding for a p115 Rho-GEF according to the invention can comprise nucleotides which occur in a naturally-occurring p115 Rho-GEF gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtained from a natural source, e.g., animal tissue and cells, body fluids, tissue culture cells, forensic samples. Naturally-occurring mutations to p115 Rho-GEF can include deletions (e.g., a truncated amino- or carboxy-terminus), substitutions, or additions of nucleotide sequence. These genes can be detected and isolated by nucleic acid hybridization according to methods which one skilled in the art would know. It is recognized that, in analogy to other oncogenes, naturally-occurring variants of p115 Rho-GEF include deletions, substitutions, and additions which produce pathological conditions in the host cell and organism.

A nucleotide sequence coding for a p115 Rho-GEF polypeptide of the invention can contain codons found in a naturally-occurring gene, transcript, or cDNA, for example, e.g., as set forth in FIG. 1 (SEQ ID NO: 1), or it can contain degenerate codons coding for the same amino acid sequences.

In addition, a nucleic acid or polypeptide of the present invention can be obtained from any desired mammalian organism, but also non-mammalian organisms. Homologs from mammalian and non-mammalian organisms can be obtained according to various methods. For example, hybridization with an oligonucleotide (see below) selective for p115 Rho-GEF can be employed to select such homologs, e.g., as described in Sambrook et al., *Molecular Cloning*, 1989, Chapter 11.

```
SAS06 X SAS13:
GAGTCTCTCTGCACCCTCTG      (SEQ ID NO:3)
CACGTCTCCGATCTCCTCGA      (SEQ ID NO:4)

MH185 X SAS11:
GGAACCGGCGGACG            (SEQ ID NO:5)
AAGATGTTCTGCAGCTCCTC.     (SEQ ID NO:6)
```

Such homologs can have varying amounts of nucleotide and amino acid sequence identity and similarity to p115 Rho-GEF. Non-mammalian organisms include, e.g., vertebrates, invertebrates, zebra fish, chicken, Drosophila, yeasts (such as *Saccharomyces cerevisiae*), *C. elegans*, roundworms, prokaryotes, plants, Arabidopsis, viruses, etc.

Modifications to a p115 Rho-GEF sequence, e.g., mutations, can also be prepared based on homology searching from gene data banks, e.g., Genbank, EMBL. Sequence homology searching can be accomplished using various methods, including algorithms described in the BLAST family of computer programs, the Smith-Waterman algorithm, etc. For example, conserved amino acids can be identified between various sequences, Dbl, lbc, Ost, 1sc, CDC24, etc. See, e.g., Touhara et al., J. Biol. Chem., 269:10217–10220, 1994; Toksoz and Williams, Oncogene, 9:621–628, 1994; Whitehead et al., J. Biol. Chem., 271:18643–18650, 1996. A mutation(s) can then be introduced into a p115 Rho-GEF sequence by identifying and aligning amino acids conserved between the polypeptides and then modifying an amino acid in a conserved or non-conserved position. A mutated p115 Rho-GEF gene can comprise conserved or nonconserved amino acids, e.g., between corresponding regions of homologous nucleic acids, especially between Dbl homology (DH) and pleckstrin homology domains, etc. For example, a mutated sequence can comprise conserved or non-conserved residues from any number of homologous sequences as mentioned-above and/or determined from an appropriate searching algorithm.

Mutations can be made in specific regions of nucleic acid coding for the p115 Rho-GEF polypeptide, e.g., in the dbl homology domain, e.g., amino acid 420–637, or the pleckstrin homology domain, e.g., amino acid 646–762, such as replacing it, changing amino acid sequences within it, etc., to analyze a function (e.g., oncogenic transformation, binding to a G-protein, guanine nucleotide exchange) of the polypeptide coded for by the nucleic acid. For example, deletion of the pleckstrin domain from amino acid 646 to amino acid 762 results in the loss of oncogenic transforming activity. The pleckstrin domain can also be involved with lipid (e.g., phosphoinositides) binding, binding to Rho, activation of the guanine nucleotide exchange activity, and localization of the polypeptide in the cell. Thus, this region can be mutagenized according to various methods and then assayed for loss or gain of the mentioned functions. The DH domain is involved with promoting GDP dissociation from the Rho GTPase. Thus, substitutions or deletions within this region can be prepared and assayed routinely for loss or gain of function. A mutation can be made in these or other regions of p115 Rho-GEF which affect its phosphorylation or protein/lipid interaction leading to its modulation of the growth signaling pathway. Such a mutated gene can be useful in various ways: for diagnosis in patients having such a mutation, to introduce into cells or animals (transgenic) as a model for a pathological condition. Mutations which affect both GEF activity and transforming activity can be analogous to those made in DH domain of the Dbl oncogene as described in Hart et al., *J. Biol. Chem.*, 269:62–65. In addition, other mutations to p115-RhoGEF include:

| LLQSIG | 560–566, conservative substitution; |
|---|---|
| VRDMEDLLRL | 606–615, Deletion; and |
| CCREILH | 594–600, Deletion. |

An inactivating mutation could comprise an alteration to the tryptophan located at residue 751 of p115-RhoGEF. Since this residue is highly conserved among many PH domain containing proteins, altering this residue could, e.g., cause improper folding, impairing its function. This mutation would inhibit the transforming activity of p115-RhoGEF, but not effect the GEF activity of p115-RhoGEF.

A nucleic acid and corresponding polypeptide of the present invention include sequences which differ from the nucleotide sequence of FIG. 1 (SEQ ID NO: 1) but which are phenotypically silent. These sequence modifications include, e.g., nucleotide substitution which do not affect the amino acid sequence (e.g., different codons for the same amino acid), replacing naturally-occurring amino acids with homologous or conservative amino acids, e.g., (based on the size of the side chain and degree of polarization) small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine. Such conservative substitutions also include those described by Dayhoff in the *Atlas of Protein Sequence and Structure* 5 (1978), and by Argos in *EMBO J.*, 8, 779–785 (1989).

A nucleic acid can comprise a nucleotide sequence coding for a polypeptide having an amino acid sequence as set forth in SEQ ID NO: 2, except where one or more positions are substituted by conservative amino acids; or a nucleotide sequence coding for a polypeptide having an amino acid sequence as set forth in SEQ ID NO:2, except having 1, 5, 10, 15, or 20 substitutions, e.g., wherein the substitutions are conservative amino acids. The invention also relates to polypeptides coded for by such nucleic acids. In addition, it may be desired to change the codons in the sequence to optimize the sequence for expression in a desired host.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNase H, improved in vivo stability, etc. See, e.g., U.S. Pat. No. 5,378,825.

Various modifications can be made to the nucleic acids, such as attaching detectable markers (avidin, biotin, radioactive elements), moieties which improve hybridization, detection, or stability. The nucleic acids can also be attached to solid supports, e.g., nitrocellulose, nylon, agarose, diazotized cellulose, latex solid microspheres, polyacrylamides, etc., according to a desired method. See, e.g., U.S. Pat. Nos. 5,470,967, 5,476,925, 5,478,893.

Another aspect of the present invention relates to oligonucleotides and nucleic acid probes. Such oligonucleotides or nucleic acid probes can be used, e.g., to detect, quantitate, or isolate a p115 Rho-GEF nucleic acid in a test sample. Detection can be desirable for a variety of different purposes, including research, diagnostic, and forensic. For diagnostic purposes, it may be desirable to identify the presence or quantity of a p115 Rho-GEF nucleic acid sequence in a sample, where the sample is obtained from tissue, cells, body fluids, etc. In a preferred method, the present invention relates to a method of detecting a p115 Rho-GEF nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR, e.g., Saiki et al., 1988, Science, 241:53; U.S. Pat. No. 4,683,202. Preferred oligonucleotides, include:

SAS06 X SAS13:
GAGTCTCTCTGCACCCTCTG    (SEQ ID NO:7)

-continued
CACGTCTCCGATCTCCTCGA    (SEQ ID NO:8)

MH185 X SAS11:
GGAACCGGCGGACG          (SEQ ID NO:9)
AAGATGTTCTGCAGCTCCTC.   (SEQ ID NO:10)

Another aspect of the present invention is a nucleotide sequence which is unique to p115 Rho-GEF. By a unique sequence to p115 Rho-GEF, it is meant a defined order of nucleotides which occurs in p115 Rho-GEF, e.g., in the nucleotide sequence of FIG. 1 (SEQ ID NO: 1), but rarely or infrequently in other nucleic acids, especially not in an animal nucleic acid, preferably mammal, such as human, rat, mouse, etc. Both sense and antisense nucleotide sequences are included. A unique nucleic acid according to the present invention can be determined routinely. A nucleic acid comprising a unique sequence of p115 Rho-GEF can be used as a hybridization probe to identify the presence of p115 Rho-GEF in a sample comprising a mixture of nucleic acids, e.g., on a Northern blot. A unique sequence includes, e.g., the c-terminal region of p115 Rho-GEF from about nucleotides 2340–3150. Hybridization can be performed under stringent conditions to select nucleic acids having at least 95% identity (i.e., complementarity) to the probe, but less stringent conditions can also be used. A unique p115 Rho-GEF nucleotide sequence can also be fused in-frame, at either its 5' or 3' end, to various nucleotide sequences as mentioned throughout the patent, including coding sequences for other parts of p115 Rho-GEF, enzymes, GFP, etc, expression control sequences, etc.

Hybridization can be performed under different conditions, depending on the desired selectivity, e.g., as described in Sambrook et al., *Molecular Cloning*, 1989. For example, to specifically detect p115 Rho-GEF, an oligonucleotide can be hybridized to a target nucleic acid under conditions in which the oligonucleotide only hybridizes to p115 Rho-GEF, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%. Since a mutation in a p115 Rho-GEF gene can cause diseases or pathological conditions, e.g., cancer, benign tumors, an oligonucleotide according to the present invention can be used diagnostically. For example, a patient having symptoms of a cancer or other condition associated with the Rho signaling pathway (see below) can be diagnosed with the disease by using an oligonucleotide according to the present invention, in polymerase chain reaction followed by DNA sequencing to identify whether the sequence is normal, in combination with other oncogene oligonucleotides, etc., e.g., p53, Rb, p21, Dbl, MTS1, Wt1, Bcl-1, Bcl-2, MDM2, etc. In a preferred method, the present invention relates to a method of diagnosing a cancer comprising contacting a sample comprising a target nucleic acid with an oligonucleotide under conditions effective to permit hybridization between the target and oligonucleotide; detecting hybridization, wherein the oligonucleotide comprises a sequence of p115 Rho-GEF, preferably a unique sequence of p115 Rho-GEF; and determining the nucleotide sequence of the target nucleic acid to which the oligonucleotide is hybridized. The sequence can be determined according to various methods, including isolating the target nucleic acid, or a cDNA thereof, and determining its sequence according to a desired method.

Oligonucleotides according to the present invention can be of any desired size, preferably 14–16 oligonucleotides in length, or more. Such oligonucleotides can have non-naturally-occurring nucleotides, e.g., inosine. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Anti-sense nucleic acid can also be prepared from a nucleic acid according to the present, preferably an anti-sense to a coding sequence of FIG. 1 (SEQ ID NO: 1). Antisense nucleic acid can be used in various ways, such as to regulate or modulate expression of p115 Rho-GEF, e.g., inhibit it, to detect its expression, or for in situ hybridization. For the purposes of regulating or modulating expression of p115 Rho-GEF, an anti-sense oligonucleotide can be operably linked to an expression control sequence.

The nucleic acid according to the present invention can be labelled according to any desired method. The nucleic acid can be labeled using radioactive tracers such as $^{32}P$, $^{35}S$, $^{125}I$, $^{3}H$, or $^{14}C$, to mention only the most commonly used tracers. The radioactive labelling can be carried out according to any method such as, for example, terminal labeling at the 3' or 5' end using a radiolabeled nucleotide, polynucleotide kinase (with or without dephosphorylation with a phosphatase) or a ligase (depending on the end to be labelled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligonucleotides, anti-sense nucleic acid, etc., can be used to detect expression of p115 Rho-GEF in whole organs, tissues, cells, etc., by various techniques, including Northern blot, PCR, in situ hybridization, etc. Such nucleic acids can be particularly useful to detect disturbed expression, e.g., cell-specific and/or subcellular alterations, of p115 Rho-GEF. The levels of p115 Rho-GEF can be determined alone or in combination with other genes products (oncogenes such as p53, Rb, Wt1, etc.), transcripts, etc. A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for the nucleic acid. Effective conditions includes any culture conditions which are suitable for achieving production of the polypeptide by the host cell, including effective temperatures, pH, medias, additives to the media in which the host cell is cultured (e.g., additives which amplify or induce expression such as butyrate, or methotrexate if the coding nucleic acid is adjacent to a dhfr gene), cyclohexamide, cell densities, culture dishes, etc. A nucleic acid can be introduced into the cell by any effective method including, e.g., calcium phosphate precipitation, electroporation, injection, DEAE-Dextran mediated transfection, fusion with liposomes, and viral transfection. A cell into which a nucleic acid of the present invention has been introduced is a transformed host cell. The nucleic acid can be extrachromosomal or integrated into a chromosome(s) of the host cell. It can be stable or transient. An expression vector is selected for its compatibility with the host cell. Host cells include, mammalian cells, e.g., COS-7, CHO, HeLa, LTK, NIH 3T3, Rat 1 fibroblasts, yeast, insect cells, such as Sf9 (S. frugipeda) and Drosophila, bacteria, such as E. coli, Streptococcus, bacillus, yeast, fungal cells, plants, embryonic stem cells (e.g., mammalian, such as mouse or human), cancer or tumor cells. Sf9 expression can be accomplished in analogy to Graziani et al., Oncogene, 7:229–235, 1992. Expression control sequences are similarly selected for host compatibility and a desired purpose, e.g., high copy number, high amounts, induction, amplification, controlled expression. Other sequences which can be employed include enhancers such as from SV40, CMV, inducible promoters, cell-type specific elements, or sequences which allow selective or specific cell expression.

In addition to a p115 Rho-GEF nucleic acid, another gene of interest can be introduced into the same host for purposes of, e.g., modulating expression p115 Rho-GEF, elucidating p115 Rho-GEF function or that of the gene of interest. Genes of interest include other oncogenes, genes involved in the cell cycle, etc. Such genes can be the normal gene, or a variation, e.g., a mutation, chimera, polymorphism, etc.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. Useful fragments include:

| | | |
|---|---|---|
| Sac1-BamH1 | nucleotides | 1454,2332, size = 878 bases; |
| Sph1-Sph1 | nucleotides | 295–1356, size = 1061 bases, and |
| Sac2-Rsr2 | nucleotides | 1696–2462, size = 766 bases. |

The p115 Rho-GEF polypeptide can also be used as a 115 kd molecular weight marker for a protein gel.

Another aspect of the present invention relates to the regulation of biological pathways in which a GTPase is involved, particularly pathological conditions, e.g., cell proliferation (e.g., cancer), growth control, morphogenesis, stress fiber formation, and integrin-mediated interactions, such as embryonic development, tumor cell growth and metastasis, programmed cell death, hemostasis, leucocyte homing and activation, bone resorption, clot retraction, and the response of cells to mechanical stress. See, e.g., Clark and Brugge, Science, 268:233–239, 1995; Bussey, Science, 272:225–226, 1996. Thus, the invention relates to all aspects of a method of modulating an activity of a Rho polypeptide comprising, administering an effective amount of a p115 Rho-GEF polypeptide or a biologically-active fragment thereof, an effective amount of a compound which modulates the activity of a Rho polypeptide, or an effective amount of a nucleic acid which codes for a p115 Rho-GEF polypeptide or a biologically-active fragment thereof. The activity of Rho which is modulated can include: GTP binding, GDP binding, GTPase activity, integrin binding, coupling or binding of Rho to receptor or effector-like molecules (such as integrins, growth factor receptors, tyrosine kinases, PI-3K, PIP-5K, etc.). See, e.g., Clark and Brugge, Science, 268:233–239, 1995. The activity can be modulated by increasing, reducing, antagonizing, promoting, etc. of Rho. The modulation of Rho can be measured by assayed routinely for GTP hydrolysis, PI(4,5) biphosphate, binding to p115 Rho-GEF, etc. An effective amount is any amount which, when administered, modulates the Rho activity. The activity can be modulated in a cell, a tissue, a whole organism, in situ, in vitro (test tube, a solid support, etc.), in vivo, or in any desired environment.

Compounds that regulate the interaction between a GEF, such p115 Rho-GEF, and a GTPase can be identified using an assay for a GEF activity, such as guanine nucleotide exchange activity, binding to a guanine nucleotide-depleted site of a GTPase, or oncogenic transforming activity, or a GTPase activity such as GTP hydrolysis. In general, a compound having such an in vitro activity will be useful in vivo to modulate a biological pathway associated with a GTPase, e.g., to treat a pathological condition associated with the biological and cellular activities mentioned above. By way of illustration, the ways in which GEF regulators can be identified are described above and below in terms of Rho and p115 Rho-GEF. However, it is to be understood that such methods can be applied generally to other GEFs.

A guanine nucleotide exchange assay, e.g., as described in Hart et al., Nature, 354:311–314, Nov. 28, 1991 (see, especially, FIG. 2 legend therein), can be used to assay for the ability of a compound to regulate the interaction between Rho and p115 Rho-GEF. For example, Rho protein (recombinant, recombinant fusion protein, or isolated from natural sources) is labeled with tritiated-GDP. The tritiated-GDP-labeled Rho is then incubated with p115 Rho-GEF and GTP under conditions in which nucleotide exchange occurs. The amount of tritiated-GDP that is retained by Rho is determined by separating bound GDP from free GDP, e.g., using a BA85 filter. The ability of a compound to regulate the interaction can be determined by adding the compound at a desired time to the incubation (e.g., before addition of p115 Rho-GEF, after addition of p115 Rho-GEF) and determining its effect on nucleotide exchange. Various agonist and antagonists of the interaction can be identified in this manner.

Binding to a guanine nucleotide-depleted site of Rho can be determined in various ways, e.g., as described in Hart et al., J. Biol. Chem., 269:62–65, 1994. Briefly, a Rho protein can be coupled to a solid support using various methods that one skilled in the art would know, e.g., using an antibody to Rho, a fusion protein between Rho and a marker protein, such as glutathione protein (GST), wherein the fusion is coupled to a solid support via the marker protein (such as glutathionine beads when GST is used), etc. The Rho protein is converted to a guanine nucleotide depleted state (for effective conditions, see, e.g., Hart et al., J. Biol. Chem., 269:62–65, 1994) and incubated with, e.g., GDP, GTPγS, and a GEF such as p115 Rho-GEF. The solid support is then separated and any protein on it run on a gel. A compound can be added at any time during the incubation (as described above) to determine its effect on the binding of the GEF to Rho.

The modulation of oncogenic transforming activity by a p115 Rho-GEF, or derivatives thereof, can be measured according to various known procedures, e.g., Eva and Aaronson, Nature, 316:273–275, 1985; Hart et al., J. Biol. Chem., 269:62–65, 1994. A compound can be added at any time during the method (e.g., pretreatment of cells; after addition of GEF, etc.) to determine its effect on the oncogenic transforming activity of p115 Rho-GEF. Various cell lines can also be used.

Other assays for Rho-mediated signal transduction can be accomplished according in analogy to procedures known in the art, e.g., as described in U.S. Pat. Nos. 5,141,851; 5,420,334; 5,436,128; and 5,482,954; WO94/16069; WO93/16179; WO91/15582; WO90/00607. In addition, peptides which inhibit the interaction, e.g., binding, between p115 Rho-GEF and a G-protein, such as RhoA, can be identified and prepared according to EP 496 162.

The present invention also relates to a method of testing for and identifying an agent which modulates the guanine nucleotide exchange activity of a guanine nucleotide exchange factor, or a biologically-active fragment thereof, or which modulates the binding between a GEF, or a biologically-active fragment thereof, and a GTPase, or a biologically-active fragment thereof, to which it binds. The method comprises contacting the GEF and GTPase with an agent to be tested and then detecting the presence or amount of binding between the GEF and GTPase, or an activity of the GEF such as guanine nucleotide exchange activity. By modulating, it is meant that addition of the agent affects the activity or binding. The binding or activity modulation can be affected in various ways, including inhibiting, blocking, preventing, increasing, enhancing, or promoting it. The binding or activity affect does not have to be achieved in a specific way, e.g., it can be competitive, noncompetitive, allosteric, sterically hindered, via cross-linking between the agent and the GEF or GTPase, etc. The agent can act on either the GEF or GTPase. The agent can be an agonist, an antagonist, or a partial agonist or antagonist. The presence or amount of binding can be determined in various ways, e.g., directly or indirectly by assaying for an activity promoted or inhibited by the GEF, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof. See, e.g., Hoeprich, Nature Biotechnology, 14:1311–1312, 1996, which describes an example of automated synthesis of organic molecules. The agent can be added simultaneously or sequentially. For example, the agent can be added to the GEF and then the resultant mixture can be further combined with the GTPase. The method can be carried out in liquid on isolated components, on a matrix (e.g., filter paper, nitrocellulose, agarose), in cells, on tissue sections, etc. In accordance with the method, a GEF can bind to the GTPase, which binding will modulate some GTPase activity. For example, as discussed above and below, a p115-RhoGEF binds to Rho, causing guanine nucleotide dissociation. The effect can be directly on the binding site between the GEF and GTPase, or it can be allosteric, or it can be on only one component (e.g., on the GEF only). Assays for guanine nucleotide dissociation can be readily adapted to identify agents which regulate the activity of a GTPase. The method further relates to obtaining or producing agents which have been identified according to the above-described method. The present invention also relates to products identified in accordance with such methods. Various GEFs and GTPases can be employed, including, p115-RhoGEF, mSOS, SOS, C3G, 1sc, Dbl, Dbl-related proteins, polypeptides comprising one or more DH domains, CDC24, Tiam, Ost, Lbc, Vav, Ect2, Bcr, Abr, Rho (A, B, and C), Rac, Ras, CDC42, chimeras thereof, biologically-active fragments thereof, muteins thereof, etc.

The present invention thus also relates to the treatment and prevention of diseases and pathological conditions associated with Rho-mediated signal transduction, e.g., cancer, diseases associated with abnormal cell proliferation. For example, the invention relates to a method of treating cancer comprising administering, to a subject in need of treatment, an amount of a compound effective to treat the disease, where the compound is a regulator of p115 Rho-GEF gene or polypeptide expression. Treating the disease can mean, delaying its onset, delaying the progression of the disease, improving or delaying clinical and pathological signs of disease. Similarly, the method also relates to treating diseases associated with inflammation, and/or the chemotactic ability of neutrophils. A regulator compound, or mixture of compounds, can be synthetic, naturally-occurring, or a combination. A regulator compound can comprise amino acids, nucleotides, hydrocarbons, lipids, polysaccharides, etc. A regulator compound is preferably a regulator of p115 Rho-GEF, e.g., inhibiting or increasing its mRNA, protein expression, or processing, or its interaction with Rho, e.g., guanine nucleotide exchange. Expression can be regulated using different agents, e.g., a polypeptide selected from amino acid 1–912 (SEQ ID NO: 2) or a derivative thereof, a ligand to the Dbl homology domain, an anti-sense nucleic acid, a ribozyme, an aptamer, a synthetic compound, or a naturally-occurring compound. Additionally, cells can be supplemented with p115 Rho-GEF, or derivatives thereof. To treat the disease, the compound, or mixture, can be formulated into pharmaceutical composition comprising a pharmaceutically acceptable carrier and other excipients as apparent to the skilled worker. See, e.g., *Remington's Pharmaceutical Sciences,* Eighteenth Edition, Mack Publishing Company, 1990. Such composition can additionally contain effective amounts of other compounds, especially for treatment of cancer.

The present invention also relates to antibodies which specifically recognize a p 115 Rho-GEF polypeptide. Antibodies, e.g., polyclonal, monoclonal, recombinant, chimeric, can be prepared according to any desired method. For example, for the production of monoclonal antibodies, a polypeptide according to FIG. 1 (SEQ ID NO: 2), can be administered to mice, goats, or rabbit subcutaneously and/or intraperitoneally, with or without adjuvant, in an amount effective to elicit an immune response. The antibodies can also be single chain or FAb. The antibodies can be IgG, subtypes, IgG2a, IgG1, etc.

An antibody specific for p115 Rho-GEF means that the antibody recognizes a defined sequence of amino acids within or including the p115 Rho-GEF amino acid sequence of FIG. 1 (SEQ ID NO: 2). Thus, a specific antibody will bind with higher affinity to an amino acid sequence, i.e., an epitope, found in FIG. 1 (SEQ ID NO: 2) than to a different epitope(s), e.g., as detected and/or measured by an immunoblot assay. Thus, an antibody which is specific for an epitope of p115 Rho-GEF is useful to detect the presence of the epitope in a sample, e.g., a sample of tissue containing p115 Rho-GEF gene product, distinguishing it from samples in which the epitope is absent. Such antibodies are useful as described in Santa Cruz Biotechnology, Inc., Research Product Catalog, can be formulated accordingly, e.g., 100 µg/ml.

In addition, ligands which bind to a p115 Rho-GEF polypeptide according to the present invention, or a derivative thereof, can also be prepared, e.g., using synthetic peptide libraries, or nucleic acid ligands (e.g., Pitrung et al., U.S. Pat. No. 5,143,854; Geysen et al., 1987, J. Immunol. Methods, 102:259–274; Scott et al., 1990, Science, 249:386; Blackwell et al., 1990, Science, 250:1104; Tuerk et al., 1990, Science, 249: 505. Nucleic acid ligands can be prepared to the Dbl homology domain (420–637) or the pleckstrin domain (646–762), etc.

Antibodies and other ligands which bind p115 Rho-GEF can be used in various ways, including as therapeutic, diagnostic, and commercial research tools, e.g, to quantitate the levels of p115 Rho-GEF polypeptide in animals, tissues, cells, etc., to identify the cellular localization and/or distribution of p115 Rho-GEF, to purify p115 Rho-GEF or a polypeptide comprising a part of p115 Rho-GEF, to modulate the function of p115 Rho-GEF, etc. Antibodies to p115 Rho-GEF, or a derivative thereof, can be used in Western blots, ELIZA, immunoprecipitation, RIA, etc. The present invention relates to such assays, compositions and kits for performing them, etc.

An antibody according to the present invention can be used to detect p115 Rho-GEF polypeptide or fragments thereof in various samples, including tissue, cells, body fluid, blood, urine, cerebrospinal fluid. A method of the present invention comprises contacting a ligand which binds to a peptide of SEQ ID NO: 2 under conditions effective, as known in the art, to achieve binding, detecting specific binding between the ligand and peptide. By specific binding, it is meant that the ligand attaches to a defined sequence of amino acids, e.g., within or including the amino acid sequence of SEQ ID NO: 2 or derivatives thereof. The antibodies or derivatives thereof can also be used to inhibit expression of p115 Rho-GEF or a fragment thereof. The levels of p115 Rho-GEF polypeptide can be determined alone or in combination with other gene products. In particular, the amount (e.g., its expression level) of p115 Rho-GEF polypeptide can be compared (e.g., as a ratio) to the amounts of other polypeptides in the same or different sample, e.g., p21, p53, Rb, WT1, etc.

A ligand for p115 Rho-GEF can be used in combination with other antibodies, e.g., antibodies that recognize oncological markers of cancer, including, Rb, p53, c-erbB-2, oncogene products, etc. In general, reagents which are specific for p115 Rho-GEF can be used in diagnostic and/or forensic studies according to any desired method, e.g., as U.S. Pat. Nos. 5,397,712; 5,434,050; 5,429,947.

The present invention also relates to a labelled p115 Rho-GEF polypeptide, prepared according to a desired method, e.g., as disclosed in U.S. Pat. No. 5,434,050. A labelled polypeptide can be used, e.g., in binding assays, such as to identify substances that bind or attach to p115 Rho-GEF, to track the movement of p115 Rho-GEF in a cell, in an in vitro, in vivo, or in situ system, etc.

A nucleic acid, polypeptide, antibody, p115 Rho-GEF ligand etc., according to the present invention can be isolated. The term "isolated" means that the material is in a form in which it is not found in its original environment, e.g., more concentrated, more purified, separated from component, etc. An isolated nucleic acid includes, e.g., a nucleic acid having the sequence of p115 Rho-GEF separated from the chromosomal DNA found in a living animal. This nucleic acid can be part of a vector or inserted into a chromosome (by specific gene-targeting or by random integration at a position other than its normal position) and still be isolated in that it is not in a form which it is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a p115 Rho-GEF nucleic acid. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082,779; 5,304,489; 5,174,986; 5,175,384; 5,175,385; 5,221,778; Gordon et al., *Proc. Natl. Acad. Sci.,* 77:7380–7384 (1980); Palmiter et al., *Cell,* 41:343–345 (1985); Palmiter et al., *Ann. Rev. Genet.,* 20:465–499 (1986); Askew et al., *Mol. Cell. Bio.,*

13:4115–4124, 1993; Games et al. *Nature*, 373:523–527, 1995; Valancius and Smithies, *Mol. Cell. Bio.*, 11:1402–1408, 1991; Stacey et al., *Mol. Cell. Bio.*, 14:1009–1016, 1994; Hasty et al., *Nature*, 350:243–246, 1995; Rubinstein et al., *Nucl. Acid Res.*, 21:2613–2617, 1993. A nucleic acid according to the present invention can be introduced into any non-human mammal, including a mouse (Hogan et al., 1986, in *Manipulating the Mouse Embryo: A Laboratory Manual*, Cold Spring Harbor Laboratory, Cold Spring Harbor, N.Y.), pig (Hammer et al., *Nature*, 315:343–345, 1985), sheep (Hammer et al., *Nature*, 315:343–345, 1985), cattle, rat, or primate. See also, e.g., Church, 1987, *Trends in Biotech.* 5:13–19; Clark et al., 1987, *Trends in Biotech.* 5:20–24; and DePamphilis et al., 1988, *BioTechniques*, 6:662–680. In addition, e.g., custom transgenic rat and mouse production is commercially available. These transgenic animals are useful as a cancer model, e.g., to test drugs, or as food for a snake.

Generally, the nucleic acids, polypeptides, antibodies, etc. of the present invention can be prepared and used as described in, U.S. Pat. Nos. 5,501,969, 5,506,133, 5,441,870; WO 90/00607; WO 91/15582;

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevir Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science;* Edited by John E. Coligan et al., John Wiley & Sons, Inc.; *Current Protocols in Immunology;* Edited by John E. Coligan et al., John Wiley & Sons, Inc.

EXAMPLES

Identification and Purification of Rho-Associated Proteins

To identify Rho associated proteins, six 10 cm dishes of 70% confluent src-transformed NIH3T3 cells were labeled overnight with 100 $\mu$Ci/ml $^{35}$S-methionine. Each plate was washed once with ice cold phosphate buffered saline (PBS) and lysed with one ml of 20 mM Tris, pH 7.5, 100 mM NaCl, 2.5 mM $MgCl_2$, 1 mM dithiothreitol, 30 $\mu$g/ml leupeptin and aprotinin, 1 mM pefabloc and 0.6% Triton X-100 (v/v). When phosphatase inhibitors were included in the lysis buffer, NaF and NaVO4 were added to final concentrations of 20 mM and 1 mM, respectively. After preclearing with GSH agarose, the supernatants were incubated with GSH agarose coupled to 10 $\mu$g of *E. coli* expressed GST-RhoA prepared in nucleotide depleted, GDP or GTP$\gamma$S states (18). For the nucleotide depleted condition, EDTA was added to the lysate to a final concentration of 10 mM. After a two hour incubation at 4° C., the beads were washed three times with phosphate-buffered saline containing 0.1% Triton X-100 and either 10 mM EDTA for the nucleotide depleted condition or 5 mM $MgCl_2$ for the GDP/GTP$\gamma$S conditions and eluted with SDS sample buffer. The eluant was analyzed on an 8%-polyacrylamide SDS gel by autoradiography. For the purification, 10 ml of cytosol was prepared from ten-15 cm plates of COS cells, which were homogenized in a hypotonic lysis buffer (20 mM Tris, pH 7.5, 10 mM NaCl, 2.5 mM $MgCl_2$, 1 mM dithiothreitol, 30 $\mu$g/ml leupeptin and aprotinin, and 1 mM pefabloc). After centrifugation, Triton X-100 was added to a final concentration of 0.2% and the lysate was then split into 2 aliquots, precleared with GSH agarose and incubated with 120 $\mu$g of either nucleotide depleted- or GDP-GST-RhoA coupled to GSH agarose and then treated as described above. To obtain peptide sequence for p115, 200 $\mu$g of nucleotide depleted GST-RhoA coupled to GSH agarose was incubated with cytosol prepared from 25–15 cm plates of COS cells. Following SDS-polyacrylamide gel electrophoresis of the proteins eluted from the beads, the stained band corresponding to p115 was excised from the gel and treated with the protease endolys-C (23).

Cloning of p115

A total of six peptides were sequenced, and one peptide, RQEVISELLVTEAAHV, was used for the purpose of obtaining a cDNA for p115. Using the rules for designing best guess oligonucleotides, the following probe, CGGCAGGAGGTGATCTCTGAGCTGCTGGTGACA GAG-GCTGCCCATGT, (SEQ ID NO: 11) was generated, end-labeled with polynucleotide kinase and used to screen $2\times10^6$ plaques from a Stratagene human fetal brain cDNA library (24). From this screening, a 3.0 kb cDNA was isolated and was found to encode a protein which contained three of the six isolated peptides. This clone, designated •N-p115, was expressed in an in vitro TNT wheat germ lectin lysate system (Promega) and was found to encode a 85 kDa protein. To find the remaining 5' coding sequence of p115, a probe, raised against the 5' end of •N-p115, was used to screen DR2 and GT11 human fetal brain cDNA libraries (Clontech). These screenings resulted in the isolation of overlapping 0.7, 0.8, 0.9 and 3.0 kb cDNAs. The cDNAs were sequenced in both directions by cycle sequencing with TAQ polymerase and analyzed on a ABI 373A DNA sequencer. To make a full-length p115 construct, the 0.7 and 3.0 kb cDNAs were digested with EcoR1 and Sfi and subcloned into the EcoR1 site of pGEM-11 Zf (Promega). This construct was used for in vitro transcription and translation in a wheat germ lectin lysate.

cDNA Constructs

For expression in the baculovirus/SF9 system, the original cDNA, •N-p115, was subcloned as a EcoRV/XbaI fragment into the Stu-XbaI sites of a pAcO vector which contains a 5' glu—glu tag. The expression and purification of the glu—glu tagged protein was performed as previously described (24). For the foci formation assays, the various p115 cDNAs, lbc and dbl cDNAs were subcloned into an EXV myc tag vector. The cDNA, which has been designated •N-p115, codes for amino acids 249 to 912 and was subcloned as a EcoRV-XbaI fragment into complementary sites of the EXV-myc vector. This construct was then used to make •N-p115•DH, in which DNA coding for amino acids 466 to 547 of the DH domain was deleted by digesting with Sac1 and Sac2. The ends of the cut plasmid were then blunted with T4 DNA polymerase, and the vector was religated. •N-p115•C was made by digesting with Rsr1 and XbaI to remove DNA which coded for amino acids 803 to 912. The construct, in which the PH domain was truncated (•N-p115•PH), was made by digesting with Ba11 and XbaI, resulting in the removal of sequence coding for amino acids 719 to 912. The methods used for making EXV-myc dbl have been described elsewhere (5).

Using primers raised against the published sequence of the lbc oncogene (22), a 500 base pair fragment was amplified from a Stratagene heart cDNA library. This fragment was then used as a template to generate a radiolabeled probe by the polymerase chain reaction. A 1.8 kb cDNA was obtained by screening the Stratagene heart cDNA library. The 1.8 kb cDNA contained sequence for the lbc oncogene as well as unpublished sequence, which probably represents proto-lbc sequence. DNA sequence, which coded for amino acids 1 to 417, was amplified by the polymerase chain reaction using specific primers. The designed primers incorporated an EcoRV and a XbaI site at the 5' and 3' ends of the amplified DNA, which was then subcloned into the EXV-myc vector.

Immunochemical Detection

Antibodies specific to p115 were raised in rabbits against a fragment of purified recombinant p115. •N-p115 (amino acids 249–912) was expressed as a glu—glu epitope tagged protein in the baculovirus insect cell system and purified by affinity chromato-graphy on anti-glu—glu Sepharose (24). Seven milligrams of glu—glu tagged •N-p115 were then coupled to CNBr-activated Sepharose and incubated with 10 mls of serum from rabbits injected with •N-p115. The antibodies were then eluted with 0.2 M glycine, pH 2.5 and neutralized with 1 M $K_2HPO_4$. For immunoblotting, affinity purified •N-p115 antibodies were used at a final concentration of 1 μg/ml. Blots were incubated overnight, washed 3 times with 25 mM Tris, pH 8.0, 150 mM NaCl, 0.05% Tween-20 and then developed with Goat anti-rabbit IgG conjugated to HRP followed by ECL detection. Monoclonal antibodies for phosphotyrosine, p190-RhoGAP and rasGAP (Transduction Labs, Inc.) were used at final concenrations of 1 μg/ml. Cross-reactivity on immunoblots was detected with goat anti-mouse IgG conjugated to HRP p115 Stimulated Dissociation from RhoA Comparison of p115 stimulated GDP and GTPγS dissociation from RhoA. Increasing amounts of glu—glu tagged •N-p115 (0, 0.02, 0.075, 0.02, 0.4, 1.0 μM) were incubated with 0.3 μM RhoA with bound [$^3$H]-GDP or GTP[$^{35}$S] for 10 minutes, and the amount of nucleotide remaining bound to RhoA was determined as described in Hart et al. (39). Specificity of •N-p115 stimulated GDP dissociation. Increasing amounts of •N-p115 (0, 0.25, 0.5, 1.0, 2.0 μM) were incubated for 5 minutes with 2.0 μM GST-RhoA, GST-Rac1, GST-Cdc42Hs or EE-K-Ras prebound with [$^3$H]-GDP and analysed as described in A. Western analysis of complex formation. One μg of glu—glu tagged •N-p115 was incubated with 4 μg of the nucleotide depleted or GDP states of baculovirus expressed GST-Rho, GST-Rac or GST-Cdc42Hs coupled to GSH agarose as described in Hart et al. (18). Proteins, which were recovered on the washed GSH beads, were analsed by SDS-PAGE and immunoblotting. The blot was probed with an affinity purified anti glu—glu monoclonal antibody. 100 ngs of glu—glu tagged •N-p115 was used as a positive control. Kinetic analysis of p115-catalyzed GEF activity on RhoA. Increasing amounts of GST-RhoA bound with GDP were incubated with 50 nM p115 in the presence of 100 μM GTP, 0.2 μM [$^{32}$P]GTP and 5 mM $MgCl_2$ for 5 minutes at room temperature. The level of GTP incorporated onto Rho/min/pmol of •N-p115 was measured as GST-RhoA[$^{32}$P]GTP bound to nitrocellulose filters.

Identification and Cloning of p115-RhoGEF

In order to identify proteins capable of interacting with Rho, GST-Rho was coupled to GSH agarose, prepared to exist in nucleotide depleted, GDP and GTPγS states, and incubated with lysates from src transformed NIH-3T3 cells metabolically labeled with $^{35}$S-methionine. The associated proteins were eluted from the agarose beads with SDS, electrophoresed on acrylamide gels and analyzed by autoradiography. By using this approach, four Rho-interacting proteins were identified: p190, p120, p130 and p115. Two proteins, p190 and p120, interacted only with GDP and GTPγS states. These two proteins were observed only when the purification was performed in the presence of phosphatase inhibitors. Anti-phosphotyrosine western analysis revealed that both p190 and p120 are tyrosine phosphorylated. Subsequent analysis with specific monoclonal antibodies demonstrated that p190 was p190-RhoGAP and p120 was RasGAP. The affinity of p190-RhoGAP for Rho-GDP/GTPγS appears to be dramatically enhanced in the presence of phosphatase inhibitors. RasGAP is also found associated with the GDP/GTPγS states, presumably via its interaction with p190-RhoGAP (25). Two more proteins, p130 and p115, also bound to Rho, but they interacted only with the nucleotide depleted (ND) state. The interaction with p130 could only be detected when phosphatase inhibitors were included in the lysis buffer, while p115 interacted with Rho independently of phosphatase inhibitors. By virtue of the ability of p130 and p115 to bind to the nucleotide depleted state of Rho, it is possible that these two proteins are GEFs for the Rho GTPase.

Using this affinity approach, p115 was purified from COS cell cytosol on a GST-Rho(ND) column. Quantities of p115 sufficient for amino acid microsequencing were gel-purified and proteolytically digested. Six peptides were isolated and sequenced. A nucleotide probe based on the sequence of one peptide was used to isolate a 3.0 kb cDNA from a human fetal brain cDNA library. Subsequent screenings resulted in the identification of three overlapping 0.7, 0.8, 0.9 and 3.0 kb cDNAs. An alignment of these sequences revealed a contiguous 3.2 kb cDNA which contained an open reading frame coding for a predicted protein of 104 kDa. Northern analysis of the expression of p115 identified two predominant transcripts with sizes of 7.0 and 3.4 kb. P115 appears to be ubiquitously expressed in human tissues but is most highly expressed in peripheral blood leukocytes, thymus and spleen. When the 3.2 kb cDNA for p115 was expressed in vitro, the protein product migrated with a molecular mass of 115 kDa. An affinity purified polyclonal antibody raised against amino acids 249–912 of p115 recognized a protein with an identical molecular weight in COS and porcine atrial endothelial (PAE) cells. P115 was also detected in many human tumor cell lines, e.g., DLD-1, HCT116, HTB177, SW480, SW620, MIA, Panc-1, HT 1080, C33A, H522, A549, and BXPC3.

Protein homology searches revealed that p115 contains a Dbl homology (DH) domain which is followed by a pleckstrin homology (PH) domain. The DH domain of p115 is 33.5%, 32.3% and 22.9% identical to analogous regions found in the Lfc, Lbc and Dbl oncogenes, respectively. The PH domain of p115 is most similar to the PH domains found in Lfc and Lbc (29.5% and 26.6% identical) and is only 9% identical to the PH domain of Dbl. The N-terminal amino acid sequence is homologous to coiled-coil containing proteins such as collagen.

Biochemical Characterization

As p115 contains a domain which is homologous to the Dbl and Lbc exchange factors, we next performed experiments to characterize the potential GEF activity of p115. Rho was prebound with $^3$H-GDP or GTP$^{35}$S and incubated with a purified recombinant form of p115 which lacked amino terminal sequence (•N-p115). The •N-p115 was more efficient in promoting the dissociation of GDP than GTPγS from RhoA and did not promote GDP dissociation from Cdc42Hs, Rac1 or K-Ras. Under appropriate conditions, the intrinsic dissociation of GDP from RhoA is stimulated 10-fold by 1 μM •N-p115. The specificity of GEF activity correlated with the ability of •N-p115 to physically associate with the nucleotide depleted state GST-Rho. •N-p115 did not interact with GST-Cdc42, GST-Rac or K-Ras. Kinetic analysis of p115-catalyzed GEF activity on Rho revealed a KM for Rho of 1.35 μM and a Vmax of 0.031 pmol incorporated GTP/min/pmol •N-p115.

Transforming Potential

Since a number of Dbl-like proteins (Dbl, Lbc, Ost) which activate Rho (18,26,27) have been shown to be transforming, we tested the transforming potentials of various myc-tagged p115 constructs, lbc and dbl (Table 1). The amount of DNA used for foci formation assays in NIH-3T3 cells was normalized based on levels of protein expression as determined by western analysis with an anti-myc tag monoclonal antibody. A nearly full-length form of p115 (amino acids 83–912) was not transforming. However, when the N-terminus was further truncated, •N-p115 was capable of inducing focus formation in NIH-3T3 cells. If this p115 construct was further truncated just C-terminal to the PH domain, •N-p115•C became more transforming. When a deletion was made inside the DH domain (•N-p115•DH) or if the PH domain was partially truncated (•Np115•PH), •N-p115 was no longer transforming (Table 1). These data are consistent with previous observations that Dbl-like proteins require intact DH and PH domains for their transforming activity (18,26,28). The transforming potentials of myc-tagged lbc and myc-tagged dbl were also tested. The results from these experiments suggest that dbl is more transforming than p115 and lbc.

It has been shown that an activated version of rho, rhoV14, also induces focus formation in NIH 3T3 cells and that the morphology of these foci differs from that of ras-induced foci (29,30). This difference presumably stems from a bifurcation in the transformation pathway downstream of Ras (31). Consistent with this interpretation, the activation of one arm of the pathway via rhoV14 synergizes with the activation of a second arm using an activated form of raf, raf-CAAX (30). The phenotype of the foci induced by •N-p115 is similar to that observed with rhoV14 and lbc. These foci contain rounded, densely packed cells. The morphology of ras or rafCAAX-induced foci have a swirling pattern, which contain spindle shaped cells (30). When rhoV14 or •N-p115 were co-transfected with rafCAAX, the majority of these foci have a morphology which is intermediate between those observed on expression of either rhoV14 or •N-p115 and expression of rafCAAX. The foci from the rhoV14/rafCAAX and the p115/rafCAAX co-transfections are dense in the middle and fusiform on the periphery. Like rhoV14, •N-p115 can synergize with the constitutively active raf-CAAX in focus formation assays. These observations are consistent with p115 acting in vivo as a GEF for Rho.

Discussion of Results

The Rho GTPase regulates the formation of actin cytoskeletal structures and other events which are important in regulating cell growth. Rho has been shown to induce the formation of stress fibers and is involved in mediating the ability of LPA and growth factors to promote stress fiber formation and the formation of focal adhesions (6). Rho appears to also control the assembly of integrin adhesion complexes which are involved in cell—cell aggregation of B-lymphocytes (32) and chemoattractant-activated leukocyte adhesion (33). Furthermore, Rho acts as a mediator of LPA and AlF$_4$ activated transcription (3) and can regulate cell growth by promoting progression through the G1 phase of the cell cycle (7). The manner by which Rho induces changes within the cell is currently not known. However, recently identified potential effectors for Rho (ROK, PKN, Rhophilin, and phospholipase-D (15,16,34,35)) may mediate the observed effects of Rho on cell morphology and transcriptional activation.

Using an affinity approach, we have been able to detect the association of four proteins with specific nucleotide states of Rho. P190-RhoGAP interacted with the GTPγS state of Rho when lysates were prepared in the absence of phosphatase inhibitors. However, if phosphatase inhibitors were included in the lysis buffer, there was a significant increase in the amount of p190 associated with the GTPγS as well as the GDP states. Under these conditions, RasGAP, which was presumably complexed to p190, was also found to be associated with the GTPγS and GDP states. The mechanism for this apparent increase in affinity of p190 for Rho is not known. It is possible that the binding of RasGAP to p190 increases its affinity for Rho. Experiments performed by McGlade et al. (36) may provide in vivo evidence to support this idea. Expression of the N-terminus of Ras-GAP (GAP-N, containing the SH3 and two SH2 domains) resulted in the formation of a stable complex with p190. Cells expressing GAP-N displayed disorganized stress fibers, bound poorly to fibronectin and had reduced focal adhesions. In these cells, the stable interaction of GAP-N with p190 may be promoting its RhoGAP activity, leading to the disappearance of cytoskeletal structures normally induced by the activation of Rho. More recently, Chang et al. (37) demonstrated that EGF treatment of cells overexpressing c-Src, induced a rapid dissolution of actin stress fibers and the appearance of p190 and RasGAP in arc-like structures that surrounded the nucleus. This suggests that p190, which is a preferred substrate for c-Src (38), is responsible for the EGF induced reduction of stress fibers. These results are consistent with a model in which tyrosine phosphorylation and RasGAP association activate the RhoGAP activity of p190.

Two other proteins which bound to the GST-Rho affinity column were p115 and p130. These two proteins interacted only with the nucleotide depleted state of Rho. P115 was purified from COS cell lysates, cloned from a human fetal brain cDNA library and found to encode a new member of the growing family of Dbl homology domain containing proteins. Accordingly, an N-terminal truncated version of p115 (•N-p115) stimulated the dissociation of GDP from Rho but not from Cdc42, Rac, or K-Ras. When lysates were prepared in the presence of phosphatase inhibitors, a second protein, p130, was also identified. P130 may represent another Rho-GEF, which may function only when phosphorylated. Alternatively, p130 may interact indirectly with Rho by coupling, in a phosphorylation dependent manner, to p115. P130 is not a hyperphosphorylated form of p115 since an antibody raised against p115 does not cross-react with p130.

Since the initial discovery that the Dbl onco-protein acted as a GEF for Cdc42Hs (39), a large number of proteins and oncogenes have been shown to contain Dbl homology (DH) domains. A feature common to all DH containing proteins is the pleckstrin domain located immediately C-terminal to the DH domain. Members of the pleckstrin family interact with the β' subunits of heterotrimeric G-proteins (40) or acidic phopholipids (41,42). The IRS-1 PTB domain structurally resembles PH domains and can interact with tyrosine phosphorylated peptides (43). Thus, PH domains may have a wide variety of cellular ligands, which may provide a mechanism of localizing Dbl-like proteins to membranes. The high degree of homology between the PH domains of Lbc and Lfc suggests they may share a common ligand, whereas the p115 PH domain deviates considerably from these sequences, suggesting it may bind to a separate ligand. A similar trend is also noted for the DH domain. Throughout this domain, Lbc and Lfc share much higher sequence identity to each other than to the DH domain of p115. Therefore, it may be appropriate to consider Lbc/Lfc and p115 as two distinct subclasses of Rho-specific GEFs. From the transformation assays performed in this paper, it is apparent that dbl is more transforming than p115. This could reflect differences in PH domain ligands, differences in GEF potencies, or perhaps differences in specificity versus Rho family members.

In this study, a variety of p115 constructs were tested for their transforming potential. A nearly full-length form of p115 (amino acids 83–912) was not transforming. However, expression of a further N-terminal truncated version (•N-p115) in NIH-3T3 cells promoted the formation of foci which were similar in phenotype to those induced by rhoV14 and also, like rhoV14, •N-p115 synergized with raf-CAAX in focus formation assays. When •N-p115 was truncated at the C-terminus (•N-p115•-C), the transforming potential of p115 was further increased, suggesting that the N- and C-termini may negatively regulate p115 function in cells. •N-p115 and •N-p115•C were tested for GEF activity and were found to possess the same levels of intrinsic GEF activities. Therefore, a C-terminal truncation may increase the transforming potential of p115 by more fully exposing its PH domain, allowing for a more efficient interaction of the PH domain with a specific ligand. Since full-length p115 has not been tested for GEF activity, it will not be possible discuss whether its inability to transform cells is due a lack of GEF activity or an unexposed, sterically hindered PH domain. Nevertheless, its lack of transforming potential suggests that important regulatory signals may be required in order for p115 to become a fully functional Rho-specific GEF in cells.

The increasing number of Dbl-like proteins, which contain a variety of structural motifs, suggests that there may be specific mechanisms to selectively regulate GEFs. Many of these motifs are involved in protein—protein interactions (44). For example, proto-Vav contains SH2 and SH3 domain (45); FGD1 (46), which is involved in Aarskog-Scott syndrome, has two potential SH3 binding sites, and ORFP (accession #D25304), which was cloned from a human immature myeloid cell line (KG1) cDNA library (17), has an SH3 domain. By coupling to other proteins, these motifs may provide a mechanism to focus the Rho-like GTPase to function in a particular cellular enviroment. Rho has been shown to participate in receptor tyrosine kinase pathways, as well as pathways, such as LPA and fMLP, which activate heterotrimeric G-proteins. Since p115 is expressed in many cultured cell lines, p115 may represent an ideal candidate to begin addressing the mechanisms which may regulate a Rho-type GEF. Considering the rather limited tissue distribution of Lbc (22), it is intriguing to speculate that p115 may mediate Rho-dependent effects in many cell types. Future studies will be aimed at determining the signalling pathways in which p115 participates, how p115 may be regulated and the proteins or lipids with which it may associate.

References

1. Boguski, M. S. and McCormick, F. (1993) *Nature* 366,643–654.

2. Coso, O. A., Chiariello, M., Yu, J. -C., Teramoto, H., Crespo, P., Xu, N., Miki, T. and Gutkind, J. S. (1995) *Cell* 81, 1137–1146.

3. Hill, C. S., Wynne, J. and Treisman, R. (1995) *Cell* 81, 1159–1170.

4. Kozma, R., Ahmed, S., Best, A. and Lim, L. (1995) *Mol. Cell. Biol.* 15, 1942–1952.

5. Minden, A., Lin, A., Claret, F. -X., Abo, A. and Karin, M. (1995) *Cell* 81, 1147–1157.

6. Nobes, C. D. and Hall, A. (1995) *Cell* 81, 53–62.

7. Olson, M. F., Ashworth, A. and Hall, A. (1995) *Science* 269, 1270–1272.

8. Barfod, E. T., Zheng, Y., Kuang, W. -J., Hart, M. J., Evans, T., Cerione, R. A. and Ashkenaz, A. (1993) *J. Biol. Chem.* 268, 26059–26062.

9. Lamarche, N. and Hall, A. (1994) *Trends Genet.* 10, 436–440.

10. Bagrodia, S., Taylor, S. J., Creasy, C. L., Chernoff, J. and Cerione, R. A. (1995) *J. Biol. Chem.* 270, 22731–22737.

11 Manser, E., Leung, T., Salihuddin, H., Zhao, Z.-s. and Lim, L. (1994) *Nature* 367, 40–46.

12. Martin, G. A., Bollag, G., McCormick, F. and Abo, A. (1995) *EMBO J.* 14, 1970–1978.

13. Moodie, S. A., Willumsen, B. M., Weber, M. J. and Wolfman, A. (1993) *Science* 260, 1658–1661.

14. Rodriguez-Viciana, P., Warne, P. H., Dhand, R., Vanhaesebroeck, B., Gout, I., Fry, M. J., Waterfield, M. D. and Downward, J. (1994) *Nature* 370, 527–532.

15. Leung, T., Manser, E., Tan, L. and Lim, L. (1995) *J. Biol. Chem.* 270, 29051–29054.

16. Watanabe, G., Saito, Y., Madaule, P., Ishizaki, T., Fujisawa, K., Morii, N., Mukai, H., Ono, Y., Kakizuki, A. and Narumiya, S. (1996) *Science* 271, 645–648.

17. Hart, M. J., Callow, M., Souza, B. and Polakis, P. (1996) *EMBO J.* 15, 2997–3005.

18. Hart, M. J., Eva, A., Zangrilli, D., Aaronson, S. A., Evans, T., Cerione, R. A. and Zheng, Y. (1994) *J. Biol. Chem.* 269, 62–65.

19. Mosteller, R. D., Han, J. and Broek, D. (1994) *Mol. Cell. Biol.* 14, 1104–1112.

20. Buday, L. and Downward, J. (1993) *Cell* 73, 611–620.

21. Eva, A. and Aaronson, S. A. (1985) *Nature* 316, 273–275.

22. Toksoz, D. and Williams, D. A. (1994) *Oncogene* 9, 621–628.

23. Totty, N. F., Waterfield, M. D. and Hsuan, J. (1992) *Protein Sci.* 1, 1215–1224.

24. Rubinfeld, B., Munemitsu, S., Clark, R., Conroy, L., Watt, K., Crosier, W. J., McCormick, F. and Polakis, P. (1991) *Cell* 65, 1033–1042.

25. Settleman, J., Narasimhan, V., Foster, L. C. and Weinberg, R. A. (1992) *Cell* 69, 539–549.

26. Horii, Y., Beeler, J. F., Sakaguchi, K., Tachibana, M. and Miki, T. (1994) *EMBO J.* 13, 4776–4786.

27. Zheng, Y., Olson, M. F., Hall, A., Cerione, R. A. and Toksoz, D. (1995) *J. Biol. Chem.* 270, 9031–9034.

28. Whitehead, I., Kirk, H., Tognon, C., Trigo-Gonzalez, G. and Kay, R. (1995) *J. Biol. Chem.* 270, 18388–18395.

29. Prendergast, G. C., Khosravi-Far, R., Solski, P. A., Kurzawa, H., Lebowitz, P. F. and Der, C. J. (1995) *Oncogene* 10, 2289–2296.

30. Qiu, R.-G., Chen, J., Kirn, D., McCormick, F. and Symons, M. (1995) *Proc. Natl. Acad. Sci. USA* 92, 11781–11785.

31. Qiu, R.-G., Chen, J., Kirn, D., McCormick, F. and Symons, M. (1995) *Nature* 374, 457–459.

32. Tominaga, T., Sugie, K., Hirata, N., Morii, N., Fukata, J., Uchida, A., Imura, H. and Narumiya, S. (1993) *J. Cell Biol.* 120, 1529–1537.

33. Laudanna, C., Campbell, J. J. and Butcher, E. C. (1996) *Science* 271, 981–983.

34. Amano, M., Mukai, H., Ono, Y., Chihara, K., Matsui, T., Hamajima, Y., Okawa, K., Iwamatsu, A. and Kaibuchi, K. (1996) *Science* 271, 648–650.

35. Malcolm, K. C., Ross, A. H., Qiu, R. -G., Symons, M. and Exton, J. H. 1994) *J. Biol. Chem.* 269, 25951–25954

36. McGlade, J., Brunkhorst, B., Anderson, D., Mbamalu, G., Settleman, J., Dedhar, S., Rozakis-Adcock, M., Chen, L. B. and Pawson, T. 1993. *EMBO J.* 12, 3073–3081.

37. Chang, J.-H., Gill, S., Settleman, J. and Parsons, S. J. 1995. *J. Cell. Biol.* 130, 355–368.

38. Chang, J.-H., Wilson, L. K., Moyers, J. S., Zhang, K. and Parsons, S. J. 1993

39. Hart, M. J., Eva, A., Evans, T., Aaronson, S. A. and Cerione, R. A. 1991. *Nature* 354, 311–314.

40. Ferguson, K. M., Lemmon, M. A., Schlessinger, J. and Sigler, P. B. 1995. *Cell* 83, 1037–1046.

41. Harlan, J. H., Hajduk, P. J., Yoon, H. S. and Fesik, S. W. 1994. *Nature* 371, 168–170.

42. Pitcher, J. A., Touhara, K., Payne, E. S. and Lefkowitz, R. J. 1995. *J. Biol. Chem.* 270, 11707–11710.

43. Zhou, M-M., Huang, B., Olejnizak, E. T., Meadows, R. P., Shuker, S. B., Miyazaki, M., Trub, T., Shoelson, S. E. and Fesik, S. W 1996 *Nature Struct. Biol.* 3, 388–393.

44. Cerione, R. A. (1996) *Curr. Opin. Cell. Biol.* In Press.

45. Khosravi-Far, R., Chrzanowska-Wodnicka, M., Solski, P. A., Eva, A., Burridge, K. and Der, C. J. 1994. *Mol. Cell. Biol.* 14, 6848–6857.

46. Pasteris, G. N., Cadle, A., Logie, L. J., Porteous, M. E. M., Schwartz, C. E., Stevenson, R. E., Glover, T. W., Wilroy, R. S. and Gorski, J. L. 1994. *Cell* 79, 669–678.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all patents and publications, cited above and in the figures are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

TABLE 1

Comparisons of the abilities of p115 constructs, lbc and dbl to promote foci formation in NIH 3T3s.

| Constructs* | Average number of foci per 10 cm plate** |
|---|---|
| 1. p115(83–912) | 0 |
| 2. ΔN-p115 | 9±1 |
| 3. ΔN-p115ΔC | 106±5 |
| 4. ΔN-p115ΔPH | 1±1 |
| 5. ΔN-p115ΔDH | 0 |
| 6. lbc | 123±4 |
| 7. dbl | 318±8 |

*The following amounts of plasmid DNA were used: 1) p115 (83–912), 5 μgs 2) ● N-p115, 0.2 μgs 3) ● N-p115 ● C, 0.2 μgs 4) ● N-p115 ● PH, 0.5 μgs 5) ● N-p115 ● DH, 2 μgs 6) lbc, 0.2 μgs 7) dbl, 0.1 μgs.
**The number of foci shown represents the average of three inde-pendent experiments, which were performed in duplicate. Foci formation assays were performed as described in Qiu et al. (31).

What is claimed:

1. An isolated p115 Rho-GEF polypeptide comprising the amino acid sequence of SEQ. ID No. 2, or a fragment thereof, wherein said fragment has a guanine nucleotide exchange (GEF) activity.

2. An isolated p115 Rho-GEF, or a fragment thereof, of claim 1, wherein said polypeptide has a guanine nucleotide exchange activity, a specific binding affinity for a guanine nucleotide depleted Rho, or a cellular oncogenic transforming activity.

3. An isolated p115 Rho-GEF, or a fragment thereof, of claim 1, which is substantially purified.

4. An isolated p115 Rho-GEE polypeptide. comprising an amino acid sequence encoded by a nucleotide sequence which hybridizes, or whose nucleic acid complement hybridizes, under stringent conditions to the nucleotide sequence set forth in SEQ ID No: 1, wherein said conditions comprise 5×SSPE, 10× Denhardts solution, 100 ug/ml salmon sperm DNA, 50% formamide 2% SDS at 42° C., or a fragment thereof wherein said polypeptide or fragment has GEF activity.

5. An isolated p115 Rho-GEF polypeptide that has GEF activity, comprising an amino acid sequence encoded by a nucleotide sequence which hybridizes, or whose nucleic acid complement hybridizes, under stringent conditions to the nucleotide sequence set forth in SEQ ID No: 1, wherein said conditions comprise 1×PAM, 0.1% SDS, 50% formamid at 42° C., or a fragment thereof wherein said polypeptide or fragment has GEF activity.

6. A composition comprising said p115 Rho-GEF polypeptides, or fragments thereof, of claims 1, 4, or 5, and a pharmaceutically acceptable carrier.

* * * * *